US010111957B2

(12) United States Patent
Cifter et al.

(10) Patent No.: US 10,111,957 B2
(45) Date of Patent: *Oct. 30, 2018

(54) INHALATION COMPOSITIONS COMPRISING GLUCOSE ANHYDROUS

(71) Applicant: Arven Ilac Sanayi Ve Ticaret A.S., Istanbul (TR)

(72) Inventors: Ümit Cifter, Istanbul (TR); Ali Turkyilmaz, Istanbul (TR); Onur Mutlu, Istanbul (TR)

(73) Assignee: Arven Ilac Snayi ve Ticaret A.S., Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 14/412,609

(22) PCT Filed: Jun. 27, 2013

(86) PCT No.: PCT/TR2013/000199
§ 371 (c)(1),
(2) Date: Jan. 2, 2015

(87) PCT Pub. No.: WO2014/007772
PCT Pub. Date: Jan. 9, 2014

(65) Prior Publication Data
US 2015/0165036 A1 Jun. 18, 2015

(30) Foreign Application Priority Data

Jul. 5, 2012 (TR) .............................. a 2012/07842
Sep. 12, 2012 (TR) .............................. a 2012/10438
Oct. 2, 2012 (TR) .............................. a 2012/11213
Jun. 18, 2013 (TR) .............................. a 2013/07336
Jun. 18, 2013 (TR) .............................. a 2013/07343

(51) Int. Cl.
A61K 9/00 (2006.01)
A61K 9/14 (2006.01)
A61K 31/137 (2006.01)
A61K 47/26 (2006.01)
A61K 45/06 (2006.01)
A61K 31/138 (2006.01)
A61K 31/167 (2006.01)
A61K 31/27 (2006.01)
A61K 31/40 (2006.01)
A61K 31/439 (2006.01)
A61K 31/4704 (2006.01)
A61K 31/538 (2006.01)
A61K 31/573 (2006.01)
A61K 31/46 (2006.01)
A61K 31/567 (2006.01)
A61K 31/58 (2006.01)

(52) U.S. Cl.
CPC ............ A61K 47/26 (2013.01); A61K 9/0075 (2013.01); A61K 9/14 (2013.01); A61K 31/137 (2013.01); A61K 31/138 (2013.01); A61K 31/167 (2013.01); A61K 31/27 (2013.01); A61K 31/40 (2013.01); A61K 31/439 (2013.01); A61K 31/46 (2013.01); A61K 31/4704 (2013.01); A61K 31/538 (2013.01); A61K 31/567 (2013.01); A61K 31/573 (2013.01); A61K 31/58 (2013.01); A61K 45/06 (2013.01)

(58) Field of Classification Search
None
See application file for complete search history.

(56) References Cited

U.S. PATENT DOCUMENTS

| 3,472,861 | A | 10/1969 | Zeile et al. |
| 3,505,337 | A | 4/1970 | Zeile et al. |
| 3,634,582 | A | 1/1972 | Hartley et al. |
| 3,929,768 | A | 12/1975 | Brattsand et al. |
| 4,335,121 | A | 6/1982 | Phillipps et al. |
| 4,817,551 | A | 4/1989 | Matson |
| 5,478,578 | A * | 12/1995 | Arnold ................ A61K 9/0075 424/489 |
| 5,482,934 | A | 1/1996 | Calatayud et al. |
| 5,990,793 | A | 11/1999 | Bieback |
| 5,993,805 | A * | 11/1999 | Sutton ................ A61K 9/0075 424/46 |
| 6,598,603 | B1 | 7/2003 | Andersson et al. |
| 6,645,466 | B1 | 11/2003 | Keller et al. |
| 2002/0055494 | A1* | 5/2002 | Hassan ............... A61K 9/0075 514/171 |
| 2002/0110529 | A1 | 8/2002 | Bechtold-Peters et al. |
| 2002/0142049 | A1* | 10/2002 | Lee ........................ B01J 2/04 424/499 |

(Continued)

FOREIGN PATENT DOCUMENTS

EP 0057401 8/1982
EP 1 124 544 B1 8/2001

(Continued)

OTHER PUBLICATIONS

U.S. Appl. No. 14/412,592, Cifter et al.
U.S. Appl. No. 14/412,595, Cifter et al.
U.S. Appl. No. 14/412,617, Cifter et al.
U.S. Appl. No. 14/412,618, Turkyilmaz et al.
U.S. Appl. No. 14/412,632, Cifter et al.
International Search Report and Written Opinion for PCT/TR2013/000212, dated Jan. 27, 2014 (9 pages).
International Search Report and Written Opinion for PCT Application No. PCT/TR2013/000196, dated Dec. 9, 2013 (10 pages).
International Search Report and Written Opinion for PCT Application No. PCT/TR2013/000197, dated Feb. 5, 2014 (9 pages).

(Continued)

Primary Examiner — Robert T. Crow
Assistant Examiner — John P Nguyen
(74) Attorney, Agent, or Firm — Liang, Frank & King LLP

(57) ABSTRACT

The invention relates to pharmaceutical powder compositions administered by means of inhalers. More particularly, it relates to pharmaceutical powder compositions having the content uniformity and the desired stability used in inhaler devices.

34 Claims, No Drawings

(56) References Cited

U.S. PATENT DOCUMENTS

| | | |
|---|---|---|
| 2003/0007932 A1* | 1/2003 | Bechtold-Peters .................. A61K 9/0075 424/46 |
| 2003/0018019 A1* | 1/2003 | Meade ................ A61K 31/537 514/171 |
| 2003/0070679 A1* | 4/2003 | Hochrainer .......... A61K 9/0075 128/203.15 |
| 2004/0009963 A1 | 1/2004 | Horstman et al. |
| 2004/0241232 A1 | 12/2004 | Brown et al. |
| 2005/0121027 A1 | 6/2005 | Nilsson et al. |
| 2005/0211244 A1 | 9/2005 | Nilsson et al. |
| 2006/0102511 A1* | 5/2006 | Pasbrig ............. A61M 15/0045 206/531 |
| 2007/0071691 A1 | 3/2007 | Brown |
| 2008/0057003 A1 | 3/2008 | Bechtold-Peters et al. |
| 2009/0076397 A1 | 3/2009 | Libbus et al. |
| 2009/0188498 A1 | 7/2009 | Thoemmes et al. |
| 2009/0209502 A1 | 8/2009 | Haeberlin et al. |
| 2009/0322513 A1 | 12/2009 | Hwang et al. |
| 2010/0055192 A1 | 3/2010 | Musa et al. |
| 2011/0105449 A1 | 5/2011 | Trofast |
| 2011/0156915 A1 | 6/2011 | Brauers et al. |
| 2012/0123277 A1 | 5/2012 | Blaha et al. |
| 2015/0157567 A1 | 6/2015 | Cifter et al. |
| 2015/0165036 A1 | 6/2015 | Cifter et al. |
| 2015/0165037 A1 | 6/2015 | Turkyilmaz et al. |
| 2015/0165038 A1 | 6/2015 | Cifter et al. |
| 2015/0173654 A1 | 6/2015 | Belanger et al. |
| 2015/0174064 A1 | 6/2015 | Cifter et al. |
| 2015/0224197 A1 | 8/2015 | Cifter et al. |
| 2016/0094700 A1 | 3/2016 | Lee et al. |
| 2016/0119424 A1 | 4/2016 | Kane et al. |
| 2016/0322078 A1 | 11/2016 | Bose et al. |

FOREIGN PATENT DOCUMENTS

| | | | |
|---|---|---|---|
| EP | 1 6111 50 | 1/2006 | |
| EP | 1 894 568 A1 | 3/2008 | |
| EP | 1944018 A1 | 7/2008 | |
| EP | 1 968 548 | 9/2008 | |
| EP | 2080508 A1 | 7/2009 | |
| EP | 2 100 599 A1 | 9/2009 | |
| EP | 2191821 A1 | 6/2010 | |
| EP | 2 239 002 B1 | 10/2010 | |
| GB | 2 434 098 | 7/2007 | |
| WO | WO 95/31964 | 11/1995 | |
| WO | WO 00/27373 | 5/2000 | |
| WO | WO 01/78693 A2 | 10/2001 | |
| WO | WO 0178693 A2 * | 10/2001 | ........... A61K 9/0075 |
| WO | WO 2004/069225 | 8/2004 | |
| WO | WO 2204/085460 A1 | 10/2004 | |
| WO | WO-2005/044187 A2 | 5/2005 | |
| WO | WO 2005/097126 A1 | 10/2005 | |
| WO | WO 2007/064912 | 6/2007 | |
| WO | WO 2007135409 A1 * | 11/2007 | ........... A61K 9/0078 |
| WO | WO-2008/000482 A1 | 1/2008 | |
| WO | WO 2008/000482 A1 | 1/2008 | |
| WO | WO-2008/066810 A2 | 6/2008 | |
| WO | WO-2008/101591 A1 | 8/2008 | |
| WO | WO-2010/144628 A2 | 12/2010 | |
| WO | WO-2011/048379 A2 | 4/2011 | |
| WO | WO-2011/076841 A2 | 6/2011 | |
| WO | WO-2011/093815 A2 | 8/2011 | |
| WO | WO-2011/093817 A1 | 8/2011 | |
| WO | WO-2011/093819 A2 | 8/2011 | |
| WO | 2011105975 A1 | 9/2011 | |
| WO | WO-2011/145109 A1 | 11/2011 | |
| WO | WO 2012/030664 A1 | 3/2012 | |
| WO | WO-2012/050945 A1 | 4/2012 | |
| WO | WO-2012/106575 A1 | 8/2012 | |
| WO | WO-2014/007769 A1 | 1/2014 | |
| WO | WO-2014/007770 A2 | 1/2014 | |
| WO | WO-2014/007771 A2 | 1/2014 | |
| WO | WO-2014/007772 A2 | 1/2014 | |
| WO | WO-2014/007773 A1 | 1/2014 | |
| WO | WO-2014/007781 A2 | 1/2014 | |

OTHER PUBLICATIONS

International Search Report and Written Opinion for PCT Application No. PCT/TR2013/000199, dated Jan. 31, 2014 (9 pages).
International Search Report and Written Opinion for PCT Application No. PCT/TR2013/000200, dated Dec. 9, 2013 (10 pages).
Search Report and Written Opinion for Turkish Patent Application No. 201207842, completed May 2, 2013 (8 pages).
Search Report and Written Opinion for Turkish Patent Application No. 201210438, completed Jan. 16, 2014 (7 pages).
Search Report and Written Opinion for Turkish Patent Application No. 201307336, completed Dec. 10, 2013 (9 pages).
Search Report and Written Opinion for Turkish Patent Application No. 201307349, completed Jan. 28, 2014 (7 pages).
Search Report and Written Opinion for Turkish Patent Application No. 201307351, completed Apr. 22, 2014 (8 pages).
Tee et al., "The use of different sugars as fine and coarse carriers for aerosolisded salbutamol sulphate," *International Journal of Pharmaceutics*, 208:111-123, 2000.
International Search Report and Written Opinion for PCT/TR2013/000198, dated Jan. 27, 2014 (9 pages).
Non-final Rejection issued in U.S. Appl. No. 14/412,609 dated Aug. 26, 2016.
Final Office Action issued in U.S. Appl. No. 14/412,609 dated Mar. 6, 2017.
Non-final Rejection issued in U.S. Appl. No. 14/412,952 dated Jun. 9, 2017.
Non-final Rejection issued in U.S. Appl. No. 12/412,595 dated May 5, 2017.
Final Office Action issued in U.S. Appl. No. 14/412,595 dated Sep. 12, 2016.
Final Office Action issued in U.S. Appl. No. 14/412,617 dated Aug. 1, 2016.
Non-final Rejection issued in U.S. Appl. No. 14/412,632 dated May 11, 2017.
International Search Report for Int'l Appl. No. PCt/TR2013/000191, dated Oct. 28, 1013.
International Search Report for lnt'l Appl. No. PCt/TR2013/000192, dated Oct. 22, 1013.
Non-final rejection issued in U.S. Appl. No. 12/412,083, dated Jul. 17, 2017.
Final Office Action issued in U.S. Appl. No. 12/412,083, dated Aug. 8, 2016.
Non-final rejection issued in U.S. Appl. No. 12/412,083, dated Apr. 27, 2016.
Non-final rejection issued in U.S. Appl. No. 14/412,066, dated Jun. 26, 2017.
Final Office Action issued in U.S. Appl. No. 14/412,066, dated Sep. 15, 2016.
Non-final rejection issued in U.S. Appl. No. 14/412,066, dated Apr. 13, 2016.
Non-final rejection issued in U.S. Appl. No. 15/088,492, dated May 16, 2017.
Final Office Action issued in U.S. Appl. No. 14/412,609, dated Mar. 6, 2007.
Cazzola et al., Pulmonary Pharmacology & Therapeutics, vol. 20, pp. 556-561 (2007).

* cited by examiner

INHALATION COMPOSITIONS COMPRISING GLUCOSE ANHYDROUS

TECHNICAL FIELD

The invention relates to pharmaceutical powder compositions administered by means of inhaler devices. More particularly, it relates to pharmaceutical powder compositions having the content uniformity and the desired stability used in inhaler devices.

BACKGROUND OF THE INVENTION

Fluticasone is an intermediate potency synthetic corticosteroid. Chemical name thereof is 6alpha,9-Difluoro-17{[(fluoromethyl)sulphonyl]carbonyl}-11beta-hydroxy-16alpha-methyl-3-oxoandrosta-1,4-diene-17alpha-yl furane-2-carboxylate and its chemical formula is as shown in formula I:

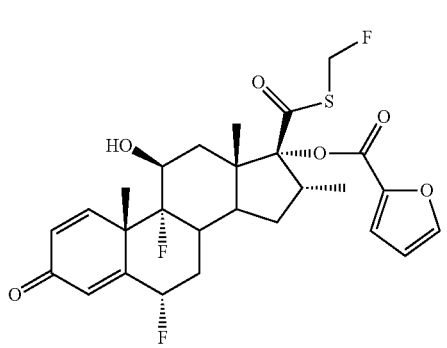

Formula 1

Fluticasone molecules are used in the treatment of allergic rhinitis, asthma and chronic obstructive pulmonary disease. It is launched onto the market under the trade name of Flixotide® with an inhaler of 60 blisters, each of which comprises 100 mcg of fluticasone propionate.

Fluticasone molecule was first disclosed in the U.S. Pat. No. 4,335,121.

WO9531964 patent application discloses a formulation comprising fluticasone propionate suitable for nebulization. Size of fluticasone particles in the formulation is smaller than 12 mm, and it further comprises one or more surfactant, one or more buffering agent and water.

WO2004069225 patent application mentions a formulation comprising fluticasone having a mean particle size smaller than 2000 nm, and at least a surface stabilizer.

This corticosteroid is administered via intranasal and oral route by inhalation for the treatment of budesonide allergic rhinitis and asthma, and via oral route for the treatment of Crohn's disease. Budesonide exhibits strong glucocorticoid and weak mineralocorticoid activity. Its chemical name is 16alpha,17alpha-butylydienedioxy-11beta,21-dihydroxy pregna-1,4-diene-3,20-dione. Chemical structure thereof is as shown in formula 2.

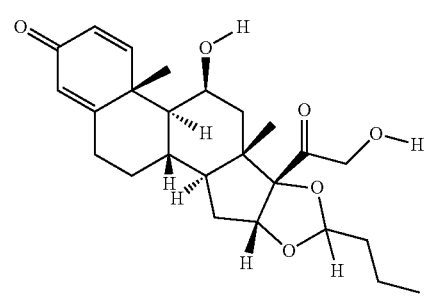

Formula 2

Budesonide is used in the treatment of allergic rhinitis, asthma and Crohn's disease. It is present in the market in the form reference dose inhaler under the name of Pulmicort®.

U.S. Pat. No. 3,929,768 is the first patent to disclose Budesonide molecule.

U.S. Pat. No. 6,598,603 patent describes a method of treatment for respiratory disorder by applying nebulized budesonide no more than once a day.

EP1124544B1 patent discloses a solid formulation applicable to nose, comprising an excipient of fine particles and medicament particles. Mass median diameter of the medicament particles is larger than that of the excipient particles. Budesonide is addressed as the active ingredient.

Mometasone is an intermediate potency corticosteroid having anti-inflammatory, anti-pruritic and vasoconstrictor properties. Its chemical name is 9alpha,21-Dichloro-11beta,17-dihydroxy-16alpha-methyl pregna-1,4-diene-3,20-dione 17-(2-furoate). Chemical structure thereof is as shown in formula 3.

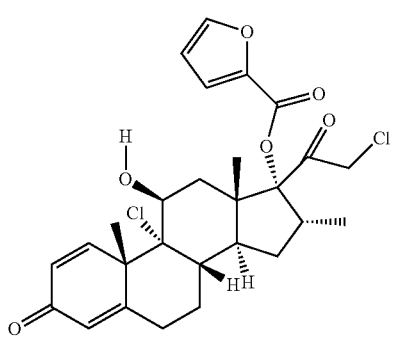

Formula 3

It has been launched onto the market under the trade name of ASMANEX®.

Mometasone molecule was first disclosed in the European patent EP0057401. European patent application EP1968548 discloses mometasone furoate particles, particle size of which is less than 200 nm and at least one surface stabilizer.

Ciclesonide is a halogen free glucocorticoid used in the treatment of inflammatory diseases such as allergic rhinitis and asthma. Chemical name thereof is {16alpha,17-[(R)-cyclohexylmethylenedioxy]-11beta-hydroxy-3,20-dioxoo-pregna-1,4-diene-21-il}isobutyrate. Chemical structure thereof is as shown in formula 4.

Formula 4

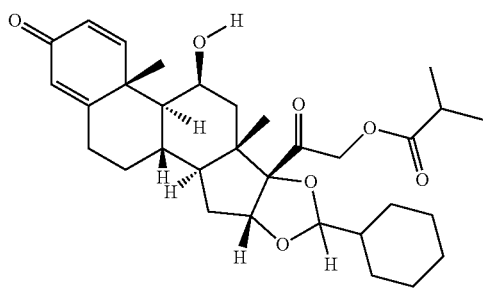

It has been launched onto the market under the trade name of ALVESCO®.

Ciclesonide molecule was first disclosed in the U.S. Pat. No. 5,482,934.

European patent application EP1611150 discloses a process regarding the preparation of ciclesonide particles, 50% of the total particle size of which are 1.8-2.0 µm.

Inhalation compositions show activity by reaching directly to the respiratory system. Contriving the compositions is based on containing the active ingredient along with the carrier and the extender having the particle sizes capable of carrying said active ingredient to the respiratory system. On the other hand, carrier particle size enabling conveying the active ingredient to the respiratory system in the desired levels is also critical. Flowing and filling of the components constituting the composition also depend on the particle size and the ratios in-between are determined accordingly. Said ratio to be in desired levels is substantially critical and the filling process rate and the amount of the formulation to be filled depend on this. Achieving the homogeneous mixture and carrying out filling of said mixture economically and in an advantageous manner in terms of process rate is a preferred condition.

It is a pre-condition for the medicament to possess content uniformity, in terms of user safety and effectiveness of the treatment. Difference of the particle sizes between the carrier and the extender used is important in order to ensure the content uniformity. This difference to be beyond measure hampers to achieve the desired content uniformity. Another potential problem is to be unable to achieve the dosage accuracy present in each cavity or capsule. And this is of vital importance in terms of effectiveness of the treatment.

In order to meet all these requirements, dry powder inhalers (DPI) should meet a series of criteria taking particularly into account the following circumstances:

Content Uniformity of the Active Drug:

Each capsule or blister should contain same amount of drug in the single dose system. Whereas in a multi-dose system, same amount of drug must be released in each application in order to ensure that the patient administers the same dosage in each time. Presence of the carrier should support the content uniformity even in a low dose drug.

Fluidity:

Design of the device, characteristics of the active ingredient and the filling platform to be used define the required properties of the carrier needed. Formulation flow characteristics have importance in terms of ensuring that the device carries out all the functions properly and provides a continuous performance. Choosing the carrier is of high importance in that it ensures that the device functions properly and carries accurate amount of active ingredient to the patient.

Therefore it is quite important to employ glucose anhydrous as the carrier, in two different particle sizes (fine and coarse).

Dose Consistency:

In order that all of the doses coming out of the device contain accurate amount of active ingredient, dry powder inhaler (DPI) devices should exhibit consistent dose uniformity. Irrespective of the inhalation capability of a patient, it is of substantial importance that the dose released from the dry powder inhaler device to be same in each time. For this reason, employing glucose anhydrous as a carrier possessing proper characteristics in the formulation assists the dose to be administered consistently.

Small drug particles are likely to agglomerate. Said coagulation can be prevented by employing suitable carrier or carrier mixtures. It also assists in controlling the fluidity of the drug coming out of the carrier device and ensuring that the active ingredient reaching to lungs is accurate and consistent.

In addition to this, the mixture of the drug particles adhered to the carrier should be homogeneous. Adhesion should be quite strong as the drug could not detach from the carrier particle. Moreover, lower doses of powder should also be filled into the device and the drug should always be released in the same way. One of the main parameters for the formulation is the particle size. Therefore, it has been found to be very important to employ the fine (small) and coarse (large) particles of the selected carrier in the formulations of the present invention in an accurate ratio.

In order to meet all these requirements, dry powder inhaler (DPI) formulations should be adapted especially by carefully choosing the employed carriers. In order to meet these requirements, the inhalable, fine or micro-fine particles of the active compounds are mixed with carriers. By means of mixing process, particle size of the carrier can be changed in order that a certain amount thereof to become inhalable. Particle size of employed carrier depends on the requirements and specifications of the powder inhaler used for application of the formulation. In this mixture, no dissociation should occur during all of the required procedures, transportation, and storage and dosing, i.e., active compound should not dissociate from its carrying particles. However, during the dissociation in the inhaler induced by inhalation of the patient, active compound particles should dissociate as effective as possible, i.e., as much as possible.

Furthermore, in the active ingredients administered via inhalation, one encounters certain stability related problems due to environmental and physical conditions. Mentioned active substances are influenced substantially by the temperature, air and humidity conditions. Exposure to air and moisture causes structural destruction of said active substances and leads them to build up a change in chemical behavior. Stability of the developed products is not in desired levels and shelf-life thereof are getting shorter. In addition, these active substances may react with auxiliary substances used along with them in the step of developing formulation. This, on the other hand, leads to impurities in the formulations and undesired compositions to get involved in the formulations. It is of critical importance for the formulation, to employ auxiliary substances and method not bringing along to mentioned problems. Moisture and air content of the active ingredients kept in the blister or capsule may be determinative for the stability. That is, the air and the moisture content within the closed blister and capsule, is quite important for these kinds of pharmaceutical forms.

For this reason, there is still a need for the carriers capable of overcoming aforementioned problems, problems related to interaction between active ingredient and carrier and moreover, problems related to pulmonary application of the drugs. Present inventions makes it possible as well, to obtain different compositions and compositions of combinations having satisfactory characteristics in a safe and effective manner, in terms of increasing the drug storing for pulmonary application or increasing the drug release rates.

As a result, there is a need for a novelty in the field relating to the compositions administrable by the patients suffering from chronic obstructive pulmonary disease or asthma.

Object and Brief Description of the Invention

Present invention relates to easily applicable inhalation compositions overcoming all of the aforementioned problems and bringing further advantages to the technical field.

Starting out from the state of the art, main object of the invention is to obtain effective and stable composition applicable in chronic obstructive pulmonary disease and asthma.

Another object of the invention is to enable a composition in which the desired filling rate and content uniformity is achieved.

Still other object of the invention is to obtain inhalation compositions having appropriate particle size and ratios ensuring to facilitate filling process into the blister package or the capsule, and enabling on the other hand to realize a homogeneous mixture.

Dry powder inhalation compositions are developed with the intent of achieving aforementioned purposes and all of the objectives that might come up from the detailed description below.

In a preferred embodiment of the invention, novelty is achieved by,
  at least one corticosteroid or a pharmaceutically acceptable salt thereof,
  fine particle lactose in the ratio of 1-20% by weight of said composition and having (d50) particle size in the range of 4-10 μm and coarse particle glucose anhydrous in the ratio of 80-99% by weight of said composition and having (d50) particle size in the range of 50-120 μm.

In a preferred embodiment of the invention, (d50) particle size of said fine particle lactose is preferably 4-7 μm.

In a preferred embodiment of the invention, particle size of said fine particle lactose (d10) is 1-5 μm, preferably 1-4 μm.

In a preferred embodiment of the invention, particle size of said fine particle lactose (d90) is 7-20 μm, preferably 7-15 μm.

In a preferred embodiment of the invention, (d50) particle size of said coarse particle glucose anhydrous is preferably 50-75 μm.

In a preferred embodiment of the invention, particle size of said coarse particle glucose anhydrous (d10) is preferably 10-50 μm.

In a preferred embodiment of the invention, particle size of said coarse particle glucose anhydrous (d90) is 120-300 μm, preferably 75-250 μm.

A preferred embodiment of the invention further comprises coarse particle lactose of (d50) particle size of 50-80 μm, preferably of 50-75 μm.

A preferred embodiment of the invention further comprises coarse particle lactose (d10) having particle size of 10-50 μm.

A preferred embodiment of the invention further comprises coarse particle lactose (d90) having particle size of 120-300 μm, preferably of 75-250 μm.

A preferred embodiment of the invention further comprises fine particle glucose anhydrous of (d50) particle size of 4-7 μm.

A preferred embodiment of the invention further comprises fine particle glucose anhydrous (d10) having particle size of 1-5 μm, preferably of 1-4 μm.

A preferred embodiment of the invention further comprises fine particle glucose anhydrous (d90) having particle size of 10-20 μm, preferably of 7-10 μm.

In a preferred embodiment of the invention, said lactose amount is preferably in the range of 1-15%, more preferably 1-10% by weight.

In a preferred embodiment of the invention, said glucose anhydrous amount is preferably in the range of 85-99%, more preferably 90-99% by weight of the composition.

In a preferred embodiment of the invention, said corticosteroid is is selected from the group consisting of at least one or a mixture of ciclesonide, budesonide, fluticasone, aldosterone, beklometazone, betametazone, chioprednol, cortisone, cortivasole, deoxycortone, desonide, desoxymetasone, dexametasone, difluorocortolone, fluchiorolone, flumetasone, flunisolide, fluquinolone, fluquinonide, flurocortisone, fluorocortolone, flurometolone, flurandrenolone, halcynonide, hydrocortisone, icometasone, meprednisone, methylprednisolone, mometasone, paramethasone, prednisolone, prednisone, tixocortole, triamcynolondane, or is a combination thereof.

In a preferred embodiment of the invention, said corticosteroid is ciclesonide.

In another preferred embodiment of the invention, said corticosteroid is budesonide.

In another preferred embodiment of the invention, said corticosteroid is fluticasone.

In another preferred embodiment of the invention, said corticosteroid is mometasone.

Another preferred embodiment of the invention further comprises one or a combination of two or more selected from β2-adrenergic agonist and muscarinic receptor antagonist.

In another preferred embodiment of the invention, said composition comprises corticosteroid and β2-adrenergic agonist.

In another preferred embodiment of the invention, said composition comprises corticosteroid and muscarinic antagonist.

In another preferred embodiment of the invention, said composition comprises corticosteroid, β2-adrenergic agonist and muscarinic receptor antagonist.

In another preferred embodiment of the invention, said muscarinic receptor antagonist is selected from the group consisting of at least one or a mixture of tiotropium, glycopyrronium, aclidinium, darotropium and ipratropium.

In a preferred embodiment of the invention, said beta-2 adrenergic agonist is selected from the group consisting of at least one or a mixture of salmeterol, ormoterol, arformoterol, salbutamol, indacaterol, terbutaline, metaproterenol, vilanterol, carmoterol, olodaterol, bambuterol, clenbuterol.

In another preferred embodiment of the invention, said retard muscarinic receptor antagonist is tiotropium.

In another preferred embodiment of the invention, said retard muscarinic receptor antagonist is glycopyrronium.

In another preferred embodiment of the invention, said retard muscarinic receptor antagonist is aclinidium.

In another preferred embodiment of the invention, said retard muscarinic receptor antagonist is darotropium.

In another preferred embodiment of the invention, said beta-2 adrenergic agonist is salmeterol.

In another preferred embodiment of the invention, said beta-2 adrenergic agonist is formoterol.

In another preferred embodiment of the invention, said beta-2 adrenergic agonist is arfomoterol.

In another preferred embodiment of the invention, said beta-2 adrenergic agonist is salbutomol.

In another preferred embodiment of the invention, said beta-2 adrenergic agonist is carmoterol.

In another preferred embodiment of the invention, said beta-2 adrenergic agonist is olodaterol.

In another preferred embodiment of the invention, said beta-2 adrenergic agonist is vilanterol.

In another preferred embodiment of the invention, said beta-2 adrenergic agonist is indacaterol.

Another preferred embodiment of the invention further comprises one of or a mixture of the excipients from glucose, mannitol, sorbitol, trehalose, cellobiose.

In another preferred embodiment of the invention, said composition comprises one of the following therapeutically active combinations:
  i. Budesonide and indacaterol,
  ii. Budesonide and oladaterol,
  iii. Budesonide and vilanterol,
  iv. Budesonide and salmeterol,
  v. Budesonide and formoterol,
  vi. Budesonide and carmoterol,
  vii. Budesonide and arformoterol In another preferred embodiment of the invention, said composition comprises one of the following therapeutically active combinations:
  i. fluticasone ve formoterol,
  ii. fluticasone ve salmeterol,
  iii. fluticasone ve vilanterol,
  iv. fluticasone ve indacaterol
  v. fluticasone ve olodaterol,
  vi. fluticasone ve carmoterol,
  vii. fluticasone ve arformoterol,
  viii. fluticasone ve salbutamol In another preferred embodiment of the invention, said composition comprises one of the following therapeutically active combinations:
  i. mometasone ve formoterol,
  ii. mometasone ve indacaterol
  iii. mometasone ve vilanterol,
  iv. mometasone ve olodaterol,
  v. mometasone ve carmoterol,
  vi. mometasone ve arformoterol,
  vii. mometasone ve salmeterol.

In another preferred embodiment of the invention, said composition comprises one of the following therapeutically active combinations:
  i. ciclesonide ve formoterol,
  ii. ciclesonide ve vilanterol,
  iii. ciclesonide ve indacaterol
  iv. ciclesonide ve olodaterol,
  v. ciclesonide ve carmoterol,
  vi. ciclesonide ve arformoterol,
  vii. ciclesonide ve salmeterol.

In another preferred embodiment of the invention, said composition comprises one of the following therapeutically active combinations:
  i. budesonide ve tiotropium,
  ii. fluticasone ve tiotropium,
  iii. mometason ve tiotropium,
  iv. ciclesonide ve tiotropium.

In another preferred embodiment of the invention, said composition comprises one of the following therapeutically active combinations:
  i. budesonide, formoterol ve tiotropium,
  ii. budesonide, salmeterol ve tiotropium,
  iii. budesonide, arformoterol ve tiotropium,
  iv. budesonide, carmoterol ve tiotropium.

In another preferred embodiment of the invention, said composition comprises one of the following therapeutically active combinations:
  i. ciclesonide, formoterol ve tiotropium,
  ii. ciclesonide, salmeterol ve tiotropium,
  iii. ciclesonide, carmoterol ve tiotropium,
  iv. ciclesonide, arformoterol ve tiotropium,
  v. ciclesonide, indacaterol ve tiotropium,
  vi. ciclesonide, olodaterol ve tiotropium,
  vii. ciclesonide, vilanterol ve tiotropium.

In another preferred embodiment of the invention, said composition comprises one of the following therapeutically active combinations:
  i. fluticasone, salmeterol ve tiotropium,
  ii. fluticasone, formoterol ve tiotropium,
  iii. fluticasone, arfomoterol ve tiotropium,
  iv. fluticasone, carmoterol ve tiotropium,
  v. fluticasone, vilanterol ve tiotropium,
  vi. fluticasone, olodaterol ve tiotropium,
  vii. fluticasone, indacaterol ve tiotropium.

In another preferred embodiment of the invention, said composition comprises one of the following therapeutically active combinations:
  i. budesonide, indacaterol ve tiotropium,
  ii. budesonide, olodaterol ve tiotropium,
  iii. budesonide, vilanterol ve tiotropium.

In another preferred embodiment of the invention, said composition comprises one of the following therapeutically active combinations:
  i. mometasone, salmeterol ve tiotropium
  ii. mometasone, formoterol ve tiotropium,
  iii. mometasone, indacaterol ve tiotropium,
  iv. mometasone, vilanterol ve tiotropium,
  v. mometasone, oladaterol ve tiotropium,
  vi. mometasone, arformoterol ve tiotropium.

In another preferred embodiment of the invention, said composition comprises one of the following therapeutically active combinations:
  i. mometasone, indacaterol ve glycopyrronium,
  ii. mometasone, salmeterol ve glycopyrronium,
  iii. mometasone, formoterol ve glycopyrronium,
  iv. mometasone, carmoterol ve glycopyrronium,
  v. mometasone, olodaterol ve glycopyrronium,
  vi. mometasone, vilanterol ve glycopyrronium.

In another preferred embodiment of the invention, said composition comprises one of the following therapeutically active combinations:
  i. fluticasone, salmeterol ve salbutamol,
  ii. fluticasone, arformeterol ve salbutamol.

Said compositions are used for the prevention or treatment of chronic obstructive pulmonary disease and asthma in mammals, especially in humans.

In another preferred embodiment of the invention, said composition comprises a blister having air and moisture barrier property, enabling simultaneous, respective and synchronic application.

In another preferred embodiment of the invention, said composition comprises a dry powder inhaler device suitable for simultaneous, respective and synchronic application in a blister and having at least one locking mechanism ensuring the device to be maintained locked in both of the positions in which it is ready for inhalation and its lid is closed and ensuring the device to be automatically re-set once the lid is closed.

In another preferred embodiment of the invention, said composition comprises a dry powder inhaler device suitable for simultaneous, respective and synchronic application in a blister.

In another preferred embodiment of the invention, pharmaceutically acceptable amount of said composition is administered one a day.

In another preferred embodiment of the invention, pharmaceutically acceptable amount of said composition is administered twice a day.

DETAILED DESCRIPTION OF INVENTION

Examples—A

| Content | % Weight (a/a) |
|---|---|
| 1- | |
| Corticosteroid | 0.1-12 |
| Lactose (fine particle) | 4.3-5.3 |
| Glucose anhydrous (coarse particle) | 84-96 |
| 2- | |
| Corticosteroid | 0.1-12 |
| Glucose anhydrous (fine particle) | 4.3-5.3 |
| Lactose (coarse particle) | 84-96 |
| 3- | |
| Corticosteroid | 0.1-12 |
| Glucose anhydrous + Lactose (fine particle) | 4.3-5.3 |
| Lactose + Glucose anhydrous (coarse particle) | 84-96 |

| | Weight and percentage amount | | | |
|---|---|---|---|---|
| Content | 25 mg | % | 5 mg | % |
| 4- | | | | |
| Ciclesonide | 0.16 | 0.64 | 0.16 | 3.2 |
| Lactose | 1.242 | 4.968 | 0.242 | 4.84 |
| Glucose anhydrous | 23.598 | 94.392 | 4.598 | 91.96 |
| TOTAL | 25 | 100 | 5 | 100 |
| 5- | | | | |
| Ciclesonide | 0.16 | 0.64 | 0.16 | 3.2 |
| Glucose anhydrous | 1.242 | 4.968 | 0.242 | 4.84 |
| Lactose | 23.598 | 94.392 | 4.598 | 91.96 |
| TOTAL | 25 | 100 | 5 | 100 |
| 6- | | | | |
| ciclesonide | 0.2 | 0.8 | 0.2 | 4 |
| Lactose | 1.24 | 4.96 | 0.24 | 4.8 |
| Glucose anhydrous | 23.56 | 94.24 | 4.56 | 91.2 |
| TOTAL | 25 | 100 | 5 | 100 |
| 7- | | | | |
| ciclesonide | 0.2 | 0.8 | 0.2 | 4 |
| Glucose anhydrous | 1.24 | 4.96 | 0.24 | 4.8 |
| Lactose | 23.56 | 94.24 | 4.56 | 91.2 |
| TOTAL | 25 | 100 | 5 | 100 |
| 8- | | | | |
| budesonide | 0.2 | 0.8 | 0.2 | 4 |
| Lactose | 1.24 | 4.96 | 0.24 | 4.8 |
| Glucose anhydrous | 23.56 | 94.24 | 4.56 | 91.2 |
| TOTAL | 25 | 100 | 5 | 100 |
| 9- | | | | |
| budesonide | 0.2 | 0.8 | 0.2 | 4 |
| Glucose anhydrous | 1.24 | 4.96 | 0.24 | 4.8 |
| Lactose | 23.56 | 94.24 | 4.56 | 91.2 |
| TOTAL | 25 | 100 | 5 | 100 |
| 10- | | | | |
| Budesonide | 0.4 | 1.6 | 0.4 | 8 |
| Lactose | 1.23 | 4.92 | 0.23 | 4.6 |
| Glucose anhydrous | 23.37 | 93.48 | 4.37 | 87.4 |
| TOTAL | 25 | 100 | 5 | 100 |
| 11- | | | | |
| Budesonide | 0.4 | 1.6 | 0.4 | 8 |
| Glucose anhydrous | 1.23 | 4.92 | 0.23 | 4.6 |
| Lactose | 23.37 | 93.48 | 4.37 | 87.4 |
| TOTAL | 25 | 100 | 5 | 100 |
| 12- | | | | |
| Mometasone | 0.1 | 0.4 | 0.1 | 2 |
| Lactose | 1.245 | 4.98 | 0.245 | 4.9 |
| Glucose anhydrous | 23.655 | 94.62 | 4.655 | 93.1 |
| TOTAL | 25 | 100 | 5 | 100 |
| 13- | | | | |
| Mometasone | 0.1 | 0.4 | 0.1 | 2 |
| Glucose anhydrous | 1.245 | 4.98 | 0.245 | 4.9 |
| Lactose | 23.655 | 94.62 | 4.655 | 93.1 |
| TOTAL | 25 | 100 | 5 | 100 |
| 14- | | | | |
| Mometasone | 0.2 | 0.8 | 0.2 | |
| Lactose | 1.24 | 4.96 | 0.24 | 4.8 |
| Glucose anhydrous | 23.56 | 94.24 | 4.56 | 91.2 |
| TOTAL | 25 | 100 | 5 | 100 |
| 15- | | | | |
| Mometasone | 0.2 | 0.8 | 0.2 | 4 |
| Glucose anhydrous | 1.24 | 4.96 | 0.24 | 4.8 |
| Lactose | 23.56 | 94.24 | 4.56 | 91.2 |
| TOTAL | 25 | 100 | 5 | 100 |
| 16- | | | | |
| Fluticasone | 0.05 | 0.2 | 0.05 | 1 |
| Lactose | 1.2475 | 4.99 | 0.2475 | 4.95 |
| Glucose anhydrous | 23.7025 | 94.81 | 4.7025 | 94.05 |
| TOTAL | 25 | 100 | 5 | 100 |

-continued

17-

| | | | | |
|---|---|---|---|---|
| Fluticasone | 0.05 | 0.2 | 0.05 | 1 |
| Glucose anhydrous | 1.2475 | 4.99 | 0.2475 | 4.95 |
| Lactose | 23.7025 | 94.81 | 4.7025 | 94.05 |
| TOTAL | 25 | 100 | 5 | 100 |

18-

| | | | | |
|---|---|---|---|---|
| Fluticasone | 0.1 | 0.4 | 0.1 | 2 |
| Lactose | 1.245 | 4.98 | 0.245 | 4.9 |
| Glucose anhydrous | 23.655 | 94.62 | 4.655 | 93.1 |
| TOTAL | 25 | 100 | 5 | 100 |

19-

| | | | | |
|---|---|---|---|---|
| Fluticasone | 0.1 | 0.4 | 0.1 | 2 |
| Glucose anhydrous | 1.245 | 4.98 | 0.245 | 4.9 |
| Lactose | 23.655 | 94.62 | 4.655 | 93.1 |
| TOTAL | 25 | 100 | 5 | 100 |

20-

| | | | | |
|---|---|---|---|---|
| Fluticasone | 0.125 | 0.5 | 0.125 | 2.5 |
| Lactose | 1.24375 | 4.975 | 0.24375 | 4.875 |
| Glucose anhydrous | 23.63125 | 94.525 | 4.63125 | 92.625 |
| TOTAL | 25 | 100 | 5 | 100 |

21-

| | | | | |
|---|---|---|---|---|
| Fluticasone | 0.125 | 0.5 | 0.125 | 2.5 |
| Glucose anhydrous | 1.24375 | 4.975 | 0.24375 | 4.875 |
| Lactose | 23.63125 | 94.525 | 4.63125 | 92.625 |
| TOTAL | 25 | 100 | 5 | 100 |

22-

| | | | | |
|---|---|---|---|---|
| Fluticasone | 0.25 | 1 | 0.25 | 5 |
| Lactose | 1.2375 | 4.95 | 0.2375 | 4.75 |
| Glucose anhydrous | 23.5125 | 94.05 | 4.5125 | 90.25 |
| TOTAL | 25 | 100 | 5 | 100 |

23-

| | | | | |
|---|---|---|---|---|
| Fluticasone | 0.25 | 1 | 0.25 | 5 |
| Glucose anhydrous | 1.2375 | 4.95 | 0.2375 | 4.75 |
| Lactose | 23.5125 | 94.05 | 4.5125 | 90.25 |
| TOTAL | 25 | 100 | 5 | 100 |

24-

| | | | | |
|---|---|---|---|---|
| Fluticasone | 0.5 | 2 | 0.5 | 10 |
| Lactose | 1.225 | 4.9 | 0.225 | 4.5 |
| Glucose anhydrous | 23.275 | 93.1 | 4.275 | 85.5 |
| TOTAL | 25 | 100 | 5 | 100 |

25-

| | | | | |
|---|---|---|---|---|
| Fluticasone | 0.5 | 2 | 0.5 | 10 |
| Glucose anhydrous | 1.225 | 4.9 | 0.225 | 4.5 |
| Lactose | 23.275 | 93.1 | 4.275 | 85.5 |
| TOTAL | 25 | 100 | 5 | 100 |

Examples—B

| Content | % Weight (a/a) |
|---|---|
| Corticosteroid | |
| β2-adrenergic agonist | |
| Lactose | |
| Glucose anhydrous | |
| excipient | |

| Content | Weight and percentage amount | | | |
|---|---|---|---|---|
| | 25 mg | % | 5 mg | % |

1-

| | | | | |
|---|---|---|---|---|
| Indacaterol | 0.15 | 0.6 | 0.15 | 3 |
| Budesonide | 0.2 | 0.8 | 0.2 | 4 |
| Lactose | 1.2325 | 4.93 | 0.2325 | 4.65 |
| Glucose anhydrous | 23.4175 | 93.67 | 4.4175 | 88.35 |
| TOTAL | 25 | | 5 | |

2-

| | | | | |
|---|---|---|---|---|
| Indacaterol | 0.15 | 0.6 | 0.15 | 3 |
| Budesonide | 0.2 | 0.8 | 0.2 | 4 |
| Glucose anhydrous | 1.2325 | 4.93 | 0.2325 | 4.65 |
| Lactose | 23.4175 | 93.67 | 4.4175 | 88.35 |
| TOTAL | 25 | | 5 | |

3-

| | | | | |
|---|---|---|---|---|
| Indacaterol | 0.15 | 0.6 | 0.15 | 3 |
| Budesonide | 0.4 | 1.6 | 0.4 | 8 |
| Lactose | 1.2225 | 4.89 | 0.2225 | 4.45 |
| Glucose anhydrous | 23.2275 | 92.91 | 4.2275 | 84.55 |
| TOTAL | 25 | | 5 | |

4-

| | | | | |
|---|---|---|---|---|
| Indacaterol | 0.15 | 0.6 | 0.15 | 3 |
| Budesonide | 0.4 | 1.6 | 0.4 | 8 |
| Glucose anhydrous | 1.2225 | 4.89 | 0.2225 | 4.45 |
| Lactose | 23.2275 | 92.91 | 4.2275 | 84.55 |
| TOTAL | 25 | | 5 | |

5-

| | | | | |
|---|---|---|---|---|
| Oladetarol | 0.005 | 0.02 | 0.005 | 0.1 |
| Budesonide | 0.2 | 0.8 | 0.2 | 4 |
| Lactose | 1.23975 | 4.959 | 0.23975 | 4.795 |
| Glucose anhydrous | 23.55525 | 94.221 | 4.55525 | 91.105 |
| TOTAL | 25 | | 5 | |

6-

| | | | | |
|---|---|---|---|---|
| Oladetarol | 0.005 | 0.02 | 0.005 | 0.1 |
| Budesonide | 0.2 | 0.8 | 0.2 | 4 |
| Glucose anhydrous | 1.23975 | 4.959 | 0.23975 | 4.795 |
| Lactose | 23.55525 | 94.221 | 4.55525 | 91.105 |
| TOTAL | 25 | | 5 | |

7-

| | | | | |
|---|---|---|---|---|
| Oladetarol | 0.005 | 0.02 | 0.005 | 0.1 |
| Budesonide | 0.4 | 1.6 | 0.4 | 8 |
| Lactose | 1.22975 | 4.919 | 0.22975 | 4.595 |
| Glucose anhydrous | 23.36525 | 93.461 | 4.36525 | 87.305 |
| TOTAL | 25 | | 5 | |

8-

| | | | | |
|---|---|---|---|---|
| Oladetarol | 0.005 | 0.02 | 0.005 | 0.1 |
| Budesonide | 0.4 | 1.6 | 0.4 | 8 |
| Glucose anhydrous | 1.22975 | 4.919 | 0.22975 | 4.595 |
| Lactose | 23.36525 | 93.461 | 4.36525 | 87.305 |
| TOTAL | 25 | | 5 | |

9-

| | | | | |
|---|---|---|---|---|
| Vilanterol | 0.025 | 0.1 | 0.025 | 0.5 |
| Budesonide | 0.2 | 0.8 | 0.2 | 4 |

-continued

| Content | mg | % | mg | % |
|---|---|---|---|---|
| Lactose | 1.23875 | 4.955 | 0.23875 | 4.775 |
| Glucose anhydrous | 23.53625 | 94.145 | 4.53625 | 90.725 |
| TOTAL | 25 | | 5 | |
| -10- | | | | |
| Vilanterol | 0.025 | 0.1 | 0.025 | 0.5 |
| Budesonide | 0.2 | 0.8 | 0.2 | 4 |
| Glucose anhydrous | 1.23875 | 4.955 | 0.23875 | 4.775 |
| Lactose | 23.53625 | 94.145 | 4.53625 | 90.725 |
| TOTAL | 25 | | 5 | |

| Content | Weight and percentage amount | | | |
|---|---|---|---|---|
| | mg | % | mg | % |
| -11- | | | | |
| Vilanterol | 0.025 | 0.1 | 0.025 | 0.5 |
| Budesonide | 0.4 | 1.6 | 0.4 | 8 |
| Lactose | 1.22875 | 4.915 | 0.22875 | 4.575 |
| Glucose anhydrous | 23.34625 | 93.385 | 4.34625 | 86.925 |
| TOTAL | 25 | | 5 | |
| -12- | | | | |
| Vilanterol | 0.025 | 0.1 | 0.025 | 0.5 |
| Budesonide | 0.4 | 1.6 | 0.4 | 8 |
| Glucose anhydrous | 1.22875 | 4.915 | 0.22875 | 4.575 |
| Lactose | 23.34625 | 93.385 | 4.34625 | 86.925 |
| TOTAL | 25 | | 5 | |

| Content | Weight and percentage amount | | | |
|---|---|---|---|---|
| | 25 mg | 25 mg | 25 mg | 25 mg |
| -13- | | | | |
| Formoterol | 0.005 | 0.02 | 0.005 | 0.1 |
| Mometasone | 0.1 | 0.4 | 0.1 | 2 |
| Lactose | 1.24475 | 4.979 | 0.24475 | 4.895 |
| Glucose anhydrous | 23.65025 | 94.601 | 4.65025 | 93.005 |
| TOTAL | 25 | | 5 | |
| -14- | | | | |
| Formoterol | 0.005 | 0.02 | 0.005 | 0.1 |
| Mometasone | 0.1 | 0.4 | 0.1 | 2 |
| Glucose anhydrous | 1.24475 | 4.979 | 0.24475 | 4.895 |
| Lactose | 23.65025 | 94.601 | 4.65025 | 93.005 |
| TOTAL | 25 | | 5 | |
| -15- | | | | |
| Formoterol | 0.005 | 0.02 | 0.005 | 0.1 |
| Mometasone | 0.2 | 0.8 | 0.2 | 4 |
| Lactose | 1.23975 | 4.959 | 0.23975 | 4.795 |
| Glucose anhydrous | 23.55525 | 94.221 | 4.55525 | 91.105 |
| TOTAL | 25 | | 5 | |
| -16- | | | | |
| Formoterol | 0.005 | 0.02 | 0.005 | 0.1 |
| Mometasone | 0.2 | 0.8 | 0.2 | 4 |
| Glucose anhydrous | 1.23975 | 4.959 | 0.23975 | 4.795 |
| Lactose | 23.55525 | 94.221 | 4.55525 | 91.105 |
| TOTAL | 25 | | 5 | |
| -17- | | | | |
| Indacaterol | 0.15 | 0.6 | 0.15 | 3 |
| Mometasone | 0.1 | 0.4 | 0.1 | 2 |
| Lactose | 1.2375 | 4.95 | 0.2375 | 4.75 |
| Glucose anhydrous | 23.5125 | 94.05 | 4.5125 | 90.25 |
| TOTAL | 25 | | 5 | |
| -18- | | | | |
| Indacaterol | 0.15 | 0.6 | 0.15 | 3 |
| Mometasone | 0.1 | 0.4 | 0.1 | 2 |
| Glucose anhydrous | 1.2375 | 4.95 | 0.2375 | 4.75 |
| Lactose | 23.5125 | 94.05 | 4.5125 | 90.25 |
| TOTAL | 25 | | 5 | |
| -19- | | | | |
| Indacaterol | 0.15 | 0.6 | 0.15 | 3 |
| Mometasone | 0.2 | 0.8 | 0.2 | 4 |
| Lactose | 1.2325 | 4.93 | 0.2325 | 4.65 |
| Glucose anhydrous | 23.4175 | 93.67 | 4.4175 | 88.35 |
| TOTAL | 25 | | 5 | |
| -20- | | | | |
| Indacaterol | 0.15 | 0.6 | 0.15 | 3 |
| Mometasone | 0.2 | 0.8 | 0.2 | 4 |
| Glucose anhydrous | 1.2325 | 4.93 | 0.2325 | 4.65 |
| Lactose | 23.4175 | 93.67 | 4.4175 | 88.35 |
| TOTAL | 25 | | 5 | |
| -21- | | | | |
| Vilanterol | 0.025 | 0.1 | 0.025 | 0.5 |
| Flutikasone | 0.1 | 0.4 | 0.1 | 2 |
| Lactose | 1.24375 | 4.975 | 0.24375 | 4.875 |
| Glucose anhydrous | 23.63125 | 94.525 | 4.63125 | 92.625 |
| TOTAL | 25 | | 5 | |
| -22- | | | | |
| Vilanterol | 0.025 | 0.1 | 0.025 | 0.5 |
| Flutikasone | 0.1 | 0.4 | 0.1 | 2 |
| Glucose anhydrous | 1.24375 | 4.975 | 0.24375 | 4.875 |
| Lactose | 23.63125 | 94.525 | 4.63125 | 92.625 |
| TOTAL | 25 | | 5 | |
| -23- | | | | |
| Salbutamol | 0.1 | 0.4 | 0.1 | 2 |
| Fluticasone | 0.5 | 2 | 0.5 | 10 |
| Lactose | 1.22 | 4.88 | 0.22 | 4.4 |
| Glucose anhydrous | 23.18 | 92.72 | 4.18 | 83.6 |
| TOTAL | 25 | | 5 | |
| -24- | | | | |
| Salbutamol | 0.1 | 0.4 | 0.1 | 2 |
| Fluticasone | 0.5 | 2 | 0.5 | 10 |
| Glucose anhydrous | 1.22 | 4.88 | 0.22 | 4.4 |
| Lactose | 23.18 | 92.72 | 4.18 | 83.6 |
| TOTAL | 25 | | 5 | |
| -25- | | | | |
| Salbutamol | 0.1 | 0.4 | 0.1 | 2 |
| Fluticasone | 0.1 | 0.4 | 0.1 | 2 |
| Lactose | 1.24 | 4.96 | 0.24 | 4.8 |
| Glucose anhydrous | 23.56 | 94.24 | 4.56 | 91.2 |
| TOTAL | 25 | | 5 | |
| -26- | | | | |
| Salbutamol | 0.1 | 0.4 | 0.1 | 2 |
| Fluticasone | 0.1 | 0.4 | 0.1 | 2 |
| Glucose anhydrous | 1.24 | 4.96 | 0.24 | 4.8 |
| Lactose | 23.56 | 94.24 | 4.56 | 91.2 |
| TOTAL | 25 | | 5 | |
| -27- | | | | |
| Salbutamol | 0.1 | 0.4 | 0.1 | 2 |
| Fluticasone | 0.25 | 1 | 0.25 | 5 |

-continued

| | | | | |
|---|---|---|---|---|
| Lactose | 1.2325 | 4.93 | 0.2325 | 4.65 |
| Glucose anhydrous | 23.4175 | 93.67 | 4.4175 | 88.35 |
| TOTAL | 25 | | 5 | |

-28-

| | | | | |
|---|---|---|---|---|
| Salbutamol | 0.1 | 0.4 | 0.1 | 2 |
| Fluticasone | 0.25 | 1 | 0.25 | 5 |
| Glucose anhydrous | 1.2325 | 4.93 | 0.2325 | 4.65 |
| Lactose | 23.4175 | 93.67 | 4.4175 | 88.35 |
| TOTAL | 25 | | 5 | |

-29-

| | | | | |
|---|---|---|---|---|
| Formoterol | 0.012 | 0.048 | 0.012 | 0.24 |
| Fluticasone | 0.1 | 0.4 | 0.1 | 2 |
| Lactose | 1.2444 | 4.9776 | 0.2444 | 4.888 |
| Glucose anhydrous | 23.6436 | 94.5744 | 4.6436 | 92.872 |
| TOTAL | 25 | | 5 | |

-30-

| | | | | |
|---|---|---|---|---|
| Formoterol | 0.012 | 0.048 | 0.012 | 0.24 |
| Fluticasone | 0.1 | 0.4 | 0.1 | 2 |
| Glucose anhydrous | 1.2444 | 4.9776 | 0.2444 | 4.888 |
| Lactose | 23.6436 | 94.5744 | 4.6436 | 92.872 |
| TOTAL | 25 | | 5 | |

-31-

| | | | | |
|---|---|---|---|---|
| Formoterol | 0.006 | 0.024 | 0.006 | 0.12 |
| Fluticasone | 0.125 | 0.5 | 0.125 | 2.5 |
| Lactose | 1.24345 | 4.9738 | 0.24345 | 4.869 |
| Glucose anhydrous | 23.62555 | 94.5022 | 4.62555 | 92.511 |
| TOTAL | 25 | | 5 | |

-32-

| | | | | |
|---|---|---|---|---|
| Formoterol | 0.006 | 0.024 | 0.006 | 0.12 |
| Fluticasone | 0.125 | 0.5 | 0.125 | 2.5 |
| Glucose anhydrous | 1.24345 | 4.9738 | 0.24345 | 4.869 |
| Lactose | 23.62555 | 94.5022 | 4.62555 | 92.511 |
| TOTAL | 25 | | 5 | |

-33-

| | | | | |
|---|---|---|---|---|
| Formoterol | 0.006 | 0.024 | 0.006 | 0.12 |
| Fluticasone | 0.25 | 1 | 0.25 | 5 |
| Lactose | 1.2372 | 4.9488 | 0.2372 | 4.744 |
| Glucose anhydrous | 23.5068 | 94.0272 | 4.5068 | 90.136 |
| TOTAL | 25 | | 5 | |

-34-

| | | | | |
|---|---|---|---|---|
| Formoterol | 0.006 | 0.024 | 0.006 | 0.12 |
| Fluticasone | 0.25 | 1 | 0.25 | 5 |
| Glucose anhydrous | 1.2372 | 4.9488 | 0.2372 | 4.744 |
| Lactose | 23.5068 | 94.0272 | 4.5068 | 90.136 |
| TOTAL | 25 | | 5 | |

-35-

| | | | | |
|---|---|---|---|---|
| Formoterol | 0.006 | 0.024 | 0.006 | 0.12 |
| Fluticasone | 0.25 | 1 | 0.25 | 5 |
| Glucose anhydrous | 1.2372 | 4.9488 | 0.2372 | 4.744 |
| Lactose | 23.5068 | 94.0272 | 4.5068 | 90.136 |
| TOTAL | 25 | | 5 | |

-36-

| | | | | |
|---|---|---|---|---|
| Formoterol | 0.012 | 0.048 | 0.012 | 0.24 |
| Fluticasone | 0.25 | 1 | 0.25 | 5 |
| Lactose | 1.2369 | 4.9476 | 0.2369 | 4.738 |
| Glucose anhydrous | 23.5011 | 94.0044 | 4.5011 | 90.022 |
| TOTAL | 25 | | 5 | |

-continued

-37-

| | | | | |
|---|---|---|---|---|
| Formoterol | 0.012 | 0.048 | 0.012 | 0.24 |
| Fluticasone | 0.25 | 1 | 0.25 | 5 |
| Glucose anhydrous | 1.2369 | 4.9476 | 0.2369 | 4.738 |
| Lactose | 23.5011 | 94.0044 | 4.5011 | 90.022 |
| TOTAL | 25 | | 5 | |

-38-

| | | | | |
|---|---|---|---|---|
| Formoterol | 0.0045 | 0.018 | 0.0045 | 0.09 |
| Ciclesonide | 0.16 | 0.64 | 0.16 | 3.2 |
| Lactose | 1.241775 | 4.9671 | 0.241775 | 4.8355 |
| Glucose anhydrous | 23.593725 | 94.3749 | 4.593725 | 91.8745 |
| TOTAL | 25 | | 5 | |

-39-

| | | | | |
|---|---|---|---|---|
| Formoterol | 0.0045 | 0.018 | 0.0045 | 0.09 |
| Ciclesonide | 0.16 | 0.64 | 0.16 | 3.2 |
| Glucose anhydrous | 1.241775 | 4.9671 | 0.241775 | 4.8355 |
| Lactose | 23.593725 | 94.3749 | 4.593725 | 91.8745 |
| TOTAL | 25 | | 5 | |

| | Weight and percentage amount | | | |
|---|---|---|---|---|
| Content | mg | % | mg | % |

-40-

| | | | | |
|---|---|---|---|---|
| Budesonide | 0.2 | 0.8 | 0.2 | 4 |
| Salmeterol | 0.05 | 0.2 | 0.05 | 1 |
| Lactose | 1.2375 | 4.95 | 0.2375 | 4.75 |
| Glucose anhydrous | 23.5125 | 94.05 | 4.5125 | 90.25 |
| TOTAL | 25 | 100 | 5 | 100 |

-41-

| | | | | |
|---|---|---|---|---|
| Budesonide | 0.4 | 1.6 | 0.4 | 8 |
| Salmeterol | 0.05 | 0.2 | 0.05 | 1 |
| Lactose | 1.2275 | 4.91 | 0.2275 | 4.55 |
| Glucose anhydrous | 23.3225 | 93.29 | 4.3225 | 86.45 |
| TOTAL | 25 | | 5 | |

-42-

| | | | | |
|---|---|---|---|---|
| Budesonide | 0.2 | 0.8 | 0.2 | 4 |
| Salmeterol | 0.05 | 0.2 | 0.05 | 1 |
| Glucose anhydrous | 1.2375 | 4.95 | 0.2375 | 4.75 |
| Lactose | 23.5125 | 94.05 | 4.5125 | 90.25 |
| TOTAL | 25 | | 5 | |

-43-

| | | | | |
|---|---|---|---|---|
| Budesonide | 0.4 | 1.6 | 0.4 | 8 |
| Salmeterol | 0.05 | 0.2 | 0.05 | 1 |
| Glucose anhydrous | 1.2275 | 4.91 | 0.2275 | 4.55 |
| Lactose | 23.3225 | 93.29 | 4.3225 | 86.45 |
| TOTAL | 25 | | 5 | |

-44-

| | | | | |
|---|---|---|---|---|
| Budesonide | 0.2 | 0.8 | 0.2 | 4 |
| Formoterol | 0.012 | 0.048 | 0.012 | 0.24 |
| Lactose | 1.2394 | 4.9576 | 0.2394 | 4.788 |
| Glucose anhydrous | 23.5486 | 94.1944 | 4.5486 | 90.972 |
| TOTAL | 25 | | 5 | |

-45-

| | | | | |
|---|---|---|---|---|
| Budesonide | 0.4 | 1.6 | 0.4 | 8 |
| Formoterol | 0.012 | 0.048 | 0.012 | 0.24 |
| Lactose | 1.2294 | 4.9176 | 0.2294 | 4.588 |
| Glucose anhydrous | 23.3586 | 93.4344 | 4.3586 | 87.172 |
| TOTAL | 25 | | 5 | |

-46-

| | | | | |
|---|---|---|---|---|
| Budesonide | 0.2 | 0.8 | 0.2 | 4 |
| Formoterol | 0.012 | 0.048 | 0.012 | 0.24 |
| Glucose anhydrous | 1.2394 | 4.9576 | 0.2394 | 4.788 |
| Lactose | 23.5486 | 94.1944 | 4.5486 | 90.972 |
| TOTAL | 25 | | 5 | |

-47-

| | | | | |
|---|---|---|---|---|
| Budesonide | 0.4 | 1.6 | 0.4 | 8 |
| Formoterol | 0.012 | 0.048 | 0.012 | 0.24 |
| Lactose | 1.2294 | 4.9176 | 0.2294 | 4.588 |
| Glucose anhydrous | 23.3586 | 93.4344 | 4.3586 | 87.172 |
| TOTAL | 25 | | 5 | |

-48-

| | | | | |
|---|---|---|---|---|
| Budesonide | 0.4 | 1.6 | 0.4 | 8 |
| Formoterol | 0.012 | 0.048 | 0.012 | 0.24 |
| Glucose anhydrous | 1.2294 | 4.9176 | 0.2294 | 4.588 |
| Lactose | 23.3586 | 93.4344 | 4.3586 | 87.172 |
| TOTAL | 25 | | 5 | |

-49-

| | | | | |
|---|---|---|---|---|
| Mometasone furoate | 0.1 | 0.4 | 0.1 | 2 |
| Oladaterol | 0.005 | 0.02 | 0.005 | 0.1 |
| Lactose | 1.24475 | 4.979 | 0.24475 | 4.895 |
| Glucose anhydrous | 23.65025 | 94.601 | 4.65025 | 93.005 |
| TOTAL | 25 | | 5 | |

-50-

| | | | | |
|---|---|---|---|---|
| Mometasone furoate | 0.2 | 0.8 | 0.2 | 4 |
| Oladaterol | 0.005 | 0.02 | 0.005 | 0.1 |
| Lactose | 1.23975 | 4.959 | 0.23975 | 4.795 |
| Glucose anhydrous | 23.55525 | 94.221 | 4.55525 | 91.105 |
| TOTAL | 25 | | 5 | |

-51-

| | | | | |
|---|---|---|---|---|
| Mometasone furoate | 0.1 | 0.4 | 0.1 | 2 |
| Oladaterol | 0.005 | 0.02 | 0.005 | 0.1 |
| Glucose anhydrous | 1.24475 | 4.979 | 0.24475 | 4.895 |
| Lactose | 23.65025 | 94.601 | 4.65025 | 93.005 |
| TOTAL | 25 | | 5 | |

-52-

| | | | | |
|---|---|---|---|---|
| Mometasone furoate | 0.2 | 0.8 | 0.2 | 4 |
| Oladaterol | 0.005 | 0.02 | 0.005 | 0.1 |
| Glucose anhydrous | 1.23975 | 4.959 | 0.23975 | 4.795 |
| Lactose | 23.55525 | 94.221 | 4.55525 | 91.105 |
| TOTAL | 25 | | 5 | |

-53-

| | | | | |
|---|---|---|---|---|
| Mometasone furoate | 0.1 | 0.4 | 0.1 | 2 |
| Arformoterol | 0.015 | 0.06 | 0.015 | 0.3 |
| Lactose | 1.24425 | 4.977 | 0.24425 | 4.885 |
| Glucose anhydrous | 23.64075 | 94.563 | 4.64075 | 92.815 |
| TOTAL | 25 | | 5 | |

-54-

| | | | | |
|---|---|---|---|---|
| Mometasone furoate | 0.2 | 0.8 | 0.2 | 4 |
| Arformoterol | 0.015 | 0.06 | 0.015 | 0.3 |
| Lactose | 1.23925 | 4.957 | 0.23925 | 4.785 |
| Glucose anhydrous | 23.54575 | 94.183 | 4.54575 | 90.915 |
| TOTAL | 25 | | 5 | |

-55-

| | | | | |
|---|---|---|---|---|
| Mometasone furoate | 0.1 | 0.4 | 0.1 | 2 |
| Arformoterol | 0.015 | 0.06 | 0.015 | 0.3 |
| Glucose anhydrous | 1.24425 | 4.977 | 0.24425 | 4.885 |
| Lactose | 23.64075 | 94.563 | 4.64075 | 92.815 |
| TOTAL | 25 | | 5 | |

-56-

| | | | | |
|---|---|---|---|---|
| Mometasone furoate | 0.2 | 0.8 | 0.2 | 4 |
| Arformoterol | 0.015 | 0.06 | 0.015 | 0.3 |
| Glucose anhydrous | 1.23925 | 4.957 | 0.23925 | 4.785 |
| Lactose | 23.54575 | 94.183 | 4.54575 | 90.915 |
| TOTAL | 25 | | 5 | |

-57-

| | | | | |
|---|---|---|---|---|
| Mometasone furoate | 0.1 | 0.4 | 0.1 | 2 |
| Salmeterol | 0.05 | 0.2 | 0.05 | 1 |
| Lactose | 1.2425 | 4.97 | 0.2425 | 4.85 |
| Glucose anhydrous | 23.6075 | 94.43 | 4.6075 | 92.15 |
| TOTAL | 25 | | 5 | |

-58-

| | | | | |
|---|---|---|---|---|
| Mometasone furoate | 0.2 | 0.8 | 0.2 | 4 |
| Salmeterol | 0.05 | 0.2 | 0.05 | 1 |
| Lactose | 1.2375 | 4.95 | 0.2375 | 4.75 |
| Glucose anhydrous | 23.5125 | 94.05 | 4.5125 | 90.25 |
| TOTAL | 25 | | 5 | |

-59-

| | | | | |
|---|---|---|---|---|
| Mometasone furoate | 0.1 | 0.4 | 0.1 | 2 |
| Salmeterol | 0.05 | 0.2 | 0.05 | 1 |
| Glucose anhydrous | 1.2425 | 4.97 | 0.2425 | 4.85 |
| Lactose | 23.6075 | 94.43 | 4.6075 | 92.15 |
| TOTAL | 25 | | 5 | |

-60-

| | | | | |
|---|---|---|---|---|
| Mometasone furoate | 0.2 | 0.8 | 0.2 | 4 |
| Salmeterol | 0.05 | 0.2 | 0.05 | 1 |
| Glucose anhydrous | 1.2375 | 4.95 | 0.2375 | 4.75 |
| Lactose | 23.5125 | 94.05 | 4.5125 | 90.25 |
| TOTAL | 25 | | 5 | |

-61-

| | | | | |
|---|---|---|---|---|
| Ciclesonide | 0.1 | 0.4 | 0.1 | 2 |
| Vilanterol | 0.025 | 0.1 | 0.025 | 0.5 |
| Lactose | 1.24375 | 4.975 | 0.24375 | 4.875 |
| Glucose anhydrous | 23.63125 | 94.525 | 4.63125 | 92.625 |
| TOTAL | 25 | | 5 | |

-62-

| | | | | |
|---|---|---|---|---|
| Ciclesonide | 0.1 | 0.4 | 0.1 | 2 |
| Vilanterol | 0.025 | 0.1 | 0.025 | 0.5 |
| Glucose anhydrous | 1.24375 | 4.975 | 0.24375 | 4.875 |
| Lactose | 23.63125 | 94.525 | 4.63125 | 92.625 |
| TOTAL | 25 | | 5 | |

| | Weight and percentage amount | | | |
|---|---|---|---|---|
| Content | 25 mg | % | 5 mg | % |

-63-

| | | | | |
|---|---|---|---|---|
| Tiotropium | 0.018 | 0.072 | 0.018 | 0.36 |
| Budesonide | 0.2 | 0.8 | 0.2 | 4 |
| Lactose | 1.2391 | 4.9564 | 0.2391 | 4.782 |
| Glucose anhydrous | 23.5429 | 94.1716 | 4.5429 | 90.858 |
| TOTAL | 25 | | 5 | |

-64-

| | | | | |
|---|---|---|---|---|
| Tiotropium | 0.018 | 0.072 | 0.018 | 0.36 |
| Budesonide | 0.2 | 0.8 | 0.2 | 4 |
| Glucose anhydrous | 1.2391 | 4.9564 | 0.2391 | 4.782 |
| Lactose | 23.5429 | 94.1716 | 4.5429 | 90.858 |
| TOTAL | 25 | | 5 | |

65-

| | | | | |
|---|---|---|---|---|
| Tiotropium | 0.018 | 0.072 | 0.018 | 0.36 |
| Budesonide | 0.4 | 1.6 | 0.4 | 8 |
| Lactose | 1.2291 | 4.9164 | 0.2291 | 4.582 |
| Glucose anhydrous | 23.3529 | 93.4116 | 4.3529 | 87.058 |
| TOTAL | 25 | | 5 | |

66-

| | | | | |
|---|---|---|---|---|
| Tiotropium | 0.018 | 0.072 | 0.018 | 0.36 |
| Budesonide | 0.4 | 1.6 | 0.4 | 8 |
| Glucose anhydrous | 1.2291 | 4.9164 | 0.2291 | 4.582 |
| Lactose | 23.3529 | 93.4116 | 4.3529 | 87.058 |
| TOTAL | 25 | | 5 | |

67-

| | | | | |
|---|---|---|---|---|
| Tiotropium | 0.018 | 0.072 | 0.018 | 0.36 |
| Fluticasone | 0.1 | 0.4 | 0.1 | 2 |
| Lactose | 1.2441 | 4.9764 | 0.2441 | 4.882 |
| Glucose anhydrous | 23.6379 | 94.5516 | 4.6379 | 92.758 |
| TOTAL | 25 | | 5 | |

68-

| | | | | |
|---|---|---|---|---|
| Tiotropium | 0.018 | 0.072 | 0.018 | 0.36 |
| Fluticasone | 0.1 | 0.4 | 0.1 | 2 |
| Glucose anhydrous | 1.2441 | 4.9764 | 0.2441 | 4.882 |
| Lactose | 23.6379 | 94.5516 | 4.6379 | 92.758 |
| TOTAL | 25 | | 5 | |

69-

| | | | | |
|---|---|---|---|---|
| Tiotropium | 0.018 | 0.072 | 0.018 | 0.36 |
| Fluticasone | 0.25 | 1 | 0.25 | 5 |
| Lactose | 1.2366 | 4.9464 | 0.2366 | 4.732 |
| Glucose anhydrous | 23.4954 | 93.9816 | 4.4954 | 89.908 |
| TOTAL | 25 | | 5 | |

70-

| | | | | |
|---|---|---|---|---|
| Tiotropium | 0.018 | 0.072 | 0.018 | 0.36 |
| Fluticasone | 0.25 | 1 | 0.25 | 5 |
| Glucose anhydrous | 1.2366 | 4.9464 | 0.2366 | 4.732 |
| Lactose | 23.4954 | 93.9816 | 4.4954 | 89.908 |
| TOTAL | 25 | | 5 | |

71-

| | | | | |
|---|---|---|---|---|
| Tiotropium | 0.018 | 0.072 | 0.018 | 0.36 |
| Fluticasone | 0.05 | 0.2 | 0.05 | 1 |
| Lactose | 1.2466 | 4.9864 | 0.2466 | 4.932 |
| Glucose anhydrous | 23.6854 | 94.7416 | 4.6854 | 93.708 |
| TOTAL | 25 | | 5 | |

72-

| | | | | |
|---|---|---|---|---|
| Tiotropium | 0.018 | 0.072 | 0.018 | 0.36 |
| Fluticasone | 0.05 | 0.2 | 0.05 | 1 |
| Glucose anhydrous | 1.2466 | 4.9864 | 0.2466 | 4.932 |
| Lactose | 23.6854 | 94.7416 | 4.6854 | 93.708 |
| TOTAL | 25 | | 5 | |

Examples—C

| Content | % Weight (a/a) |
|---|---|
| Corticosteroid | |
| β-adrenergic agonist | |
| Anticholinergic | |
| Lactose | |
| Glucose anhydrous | |
| excipient | |

| | Weight and percentage amount | | | |
|---|---|---|---|---|
| Content | mg | % | mg | % |

1-

| | | | | |
|---|---|---|---|---|
| Budesonide | 0.2 | 0.8 | 0.2 | 4 |
| Formoterol | 0.012 | 0.048 | 0.012 | 0.24 |
| Tiotropium | 0.018 | 0.072 | 0.018 | 0.36 |
| Lactose | 1.2385 | 4.954 | 0.2385 | 4.77 |
| Glucose anhydrous | 23.5315 | 94.126 | 4.5315 | 90.63 |
| TOTAL | 25 | 100 | 5 | 100 |

2-

| | | | | |
|---|---|---|---|---|
| Budesonide | 0.2 | 0.8 | 0.2 | 4 |
| Formoterol | 0.012 | 0.048 | 0.012 | 0.24 |
| Tiotropium | 0.018 | 0.072 | 0.018 | 0.36 |
| Glucose anhydrous | 1.2385 | 4.954 | 0.2385 | 4.77 |
| Lactose | 23.5315 | 94.126 | 4.5315 | 90.63 |
| TOTAL | 25 | | 5 | |

3-

| | | | | |
|---|---|---|---|---|
| Budesonide | 0.4 | 1.6 | 0.4 | 8 |
| Formoterol | 0.012 | 0.048 | 0.012 | 0.24 |
| Tiotropium | 0.018 | 0.072 | 0.018 | 0.36 |
| Lactose | 1.2285 | 4.914 | 0.2285 | 4.57 |
| Glucose anhydrous | 23.3415 | 93.366 | 4.3415 | 86.83 |
| TOTAL | 25 | 100 | 5 | 100 |

4-

| | | | | |
|---|---|---|---|---|
| Budesonide | 0.4 | 1.6 | 0.4 | 8 |
| Formoterol | 0.012 | 0.048 | 0.012 | 0.24 |
| Tiotropium | 0.018 | 0.072 | 0.018 | 0.36 |
| Glucose anhydrous | 1.2285 | 4.914 | 0.2285 | 4.57 |
| Lactose | 23.3415 | 93.366 | 4.3415 | 86.83 |
| TOTAL | 25 | | 5 | |

5-

| | | | | |
|---|---|---|---|---|
| Ciclesonide | 0.2 | 0.8 | 0.2 | 4 |
| Formoterol | 0.006 | 0.024 | 0.006 | 0.12 |
| Tiotropium | 0.009 | 0.036 | 0.009 | 0.18 |
| Lactose | 1.23925 | 4.957 | 0.23925 | 4.785 |
| Glucose anhydrous | 23.54575 | 94.183 | 4.54575 | 90.915 |
| TOTAL | 25 | | 5 | |

6-

| | | | | |
|---|---|---|---|---|
| Ciclesonide | 0.2 | 0.8 | 0.2 | 4 |
| Formoterol | 0.006 | 0.024 | 0.006 | 0.12 |
| Tiotropium | 0.018 | 0.072 | 0.018 | 0.36 |
| Glucose anhydrous | 1.2388 | 4.9552 | 0.2388 | 4.776 |
| Lactose | 23.5372 | 94.1488 | 4.5372 | 90.744 |
| TOTAL | 25 | | 5 | |

7-

| | | | | |
|---|---|---|---|---|
| Fluticasone | 0.1 | 0.4 | 0.1 | 2 |
| salmeterol | 0.05 | 0.2 | 0.05 | 1 |

-continued

| | | | | |
|---|---|---|---|---|
| Tiotropium | 0.018 | 0.072 | 0.018 | 0.36 |
| Lactose | 1.2416 | 4.9664 | 0.2416 | 4.832 |
| Glucose anhydrous | 23.5904 | 94.3616 | 4.5904 | 91.808 |
| TOTAL | 25 | | 5 | |

8-

| | | | | |
|---|---|---|---|---|
| Fluticasone | 0.1 | 0.4 | 0.1 | 2 |
| salmeterol | 0.05 | 0.2 | 0.05 | 1 |
| Tiotropium | 0.018 | 0.072 | 0.018 | 0.36 |
| Glucose anhydrous | 1.2416 | 4.9664 | 0.2416 | 4.832 |
| Lactose | 23.5904 | 94.3616 | 4.5904 | 91.808 |
| TOTAL | 25 | | 5 | |

9-

| | | | | |
|---|---|---|---|---|
| Fluticasone | 0.25 | 1 | 0.25 | 5 |
| salmeterol | 0.05 | 0.2 | 0.05 | 1 |
| Tiotropium | 0.018 | 0.072 | 0.018 | 0.36 |
| Lactose | 1.2341 | 4.9364 | 0.2341 | 4.682 |
| Glucose anhydrous | 23.4479 | 93.7916 | 4.4479 | 88.958 |
| TOTAL | 25 | | 5 | |

10-

| | | | | |
|---|---|---|---|---|
| Fluticasone | 0.25 | 1 | 0.25 | 5 |
| salmeterol | 0.05 | 0.2 | 0.05 | 1 |
| Tiotropium | 0.018 | 0.072 | 0.018 | 0.36 |
| Glucose anhydrous | 1.2341 | 4.9364 | 0.2341 | 4.682 |
| Lactose | 23.4479 | 93.7916 | 4.4479 | 88.958 |
| TOTAL | 25 | | 5 | |

11-

| | | | | |
|---|---|---|---|---|
| Fluticasone | 0.05 | 0.2 | 0.05 | 1 |
| salmeterol | 0.05 | 0.2 | 0.05 | 1 |
| Tiotropium | 0.018 | 0.072 | 0.018 | 0.36 |
| Lactose | 1.2441 | 4.9764 | 0.2441 | 4.882 |
| Glucose anhydrous | 23.6379 | 94.5516 | 4.6379 | 92.758 |
| TOTAL | 25 | | 5 | |

12-

| | | | | |
|---|---|---|---|---|
| Fluticasone | 0.05 | 0.2 | 0.05 | 1 |
| salmeterol | 0.05 | 0.2 | 0.05 | 1 |
| Tiotropium | 0.018 | 0.072 | 0.018 | 0.36 |
| Glucose anhydrous | 1.2441 | 4.9764 | 0.2441 | 4.882 |
| Lactose | 23.6379 | 94.5516 | 4.6379 | 92.758 |
| TOTAL | 25 | | 5 | |

13-

| | | | | |
|---|---|---|---|---|
| Fluticasone | 0.1 | 0.4 | 0.1 | 2 |
| Arformeterol | 0.015 | 0.06 | 0.015 | 0.3 |
| Tiotropium | 0.018 | 0.072 | 0.018 | 0.36 |
| Lactose | 1.24335 | 4.9734 | 0.24335 | 4.867 |
| Glucose anhydrous | 23.62365 | 94.4946 | 4.62365 | 92.473 |
| TOTAL | 25 | | 5 | |

14-

| | | | | |
|---|---|---|---|---|
| Fluticasone | 0.1 | 0.4 | 0.1 | 2 |
| Arformeterol | 0.015 | 0.06 | 0.015 | 0.3 |
| Tiotropium | 0.018 | 0.072 | 0.018 | 0.36 |
| Glucose anhydrous | 1.24335 | 4.9734 | 0.24335 | 4.867 |
| Lactose | 23.62365 | 94.4946 | 4.62365 | 92.473 |
| TOTAL | 25 | | 5 | |

-continued

15-

| | | | | |
|---|---|---|---|---|
| Fluticasone | 0.25 | 1 | 0.25 | 5 |
| Arformeterol | 0.015 | 0.06 | 0.015 | 0.3 |
| Tiotropium | 0.018 | 0.072 | 0.018 | 0.36 |
| Lactose | 1.23585 | 4.9434 | 0.23585 | 4.717 |
| Glucose anhydrous | 23.48115 | 93.9246 | 4.48115 | 89.623 |
| TOTAL | 25 | | 5 | |

16-

| | | | | |
|---|---|---|---|---|
| Fluticasone | 0.25 | 1 | 0.25 | 5 |
| Arformeterol | 0.015 | 0.06 | 0.015 | 0.3 |
| Tiotropium | 0.018 | 0.072 | 0.018 | 0.36 |
| Glucose anhydrous | 1.23585 | 4.9434 | 0.23585 | 4.717 |
| Lactose | 23.48115 | 93.9246 | 4.48115 | 89.623 |
| TOTAL | 25 | | 5 | |

17-

| | | | | |
|---|---|---|---|---|
| Fluticasone | 0.05 | 0.2 | 0.05 | 1 |
| Arformeterol | 0.015 | 0.06 | 0.015 | 0.3 |
| Tiotropium | 0.018 | 0.072 | 0.018 | 0.36 |
| Lactose | 1.24585 | 4.9834 | 0.24585 | 4.917 |
| Glucose anhydrous | 23.67115 | 94.6846 | 4.67115 | 93.423 |
| TOTAL | 25 | | 5 | |

18-

| | | | | |
|---|---|---|---|---|
| Fluticasone | 0.05 | 0.2 | 0.05 | 1 |
| Arformeterol | 0.015 | 0.06 | 0.015 | 0.3 |
| Tiotropium | 0.018 | 0.072 | 0.018 | 0.36 |
| Glucose anhydrous | 1.24585 | 4.9834 | 0.24585 | 4.917 |
| Lactose | 23.67115 | 94.6846 | 4.67115 | 93.423 |
| TOTAL | 25 | | 5 | |

19-

| | | | | |
|---|---|---|---|---|
| Fluticasone | 0.1 | 0.4 | 0.1 | 2 |
| Indacaterol | 0.15 | 0.6 | 0.15 | 3 |
| Tiotropium | 0.018 | 0.072 | 0.018 | 0.36 |
| Lactose | 1.2366 | 4.9464 | 0.2366 | 4.732 |
| Glucose anhydrous | 23.4954 | 93.9816 | 4.4954 | 89.908 |
| TOTAL | 25 | | 5 | |

20-

| | | | | |
|---|---|---|---|---|
| Fluticasone | 0.1 | 0.4 | 0.1 | 2 |
| Indacaterol | 0.15 | 0.6 | 0.15 | 3 |
| Tiotropium | 0.018 | 0.072 | 0.018 | 0.36 |
| Glucose anhydrous | 1.2366 | 4.9464 | 0.2366 | 4.732 |
| Lactose | 23.4954 | 93.9816 | 4.4954 | 89.908 |
| TOTAL | 25 | | 5 | |

21-

| | | | | |
|---|---|---|---|---|
| Fluticasone | 0.25 | 1 | 0.25 | 5 |
| Indacaterol | 0.15 | 0.6 | 0.15 | 3 |
| Tiotropium | 0.018 | 0.072 | 0.018 | 0.36 |
| Lactose | 1.2291 | 4.9164 | 0.2291 | 4.582 |
| Glucose anhydrous | 23.3529 | 93.4116 | 4.3529 | 87.058 |
| TOTAL | 25 | | 5 | |

22-

| | | | | |
|---|---|---|---|---|
| Fluticasone | 0.25 | 1 | 0.25 | 5 |
| Indacaterol | 0.15 | 0.6 | 0.15 | 3 |
| Tiotropium | 0.018 | 0.072 | 0.018 | 0.36 |

-continued

| | | | | |
|---|---|---|---|---|
| Glucose anhydrous | 1.2291 | 4.9164 | 0.2291 | 4.582 |
| Lactose | 23.3529 | 93.4116 | 4.3529 | 87.058 |
| TOTAL 23- | 25 | | 5 | |
| Fluticasone | 0.05 | 0.2 | 0.05 | 1 |
| Indacaterol | 0.15 | 0.6 | 0.15 | 3 |
| Tiotropium | 0.018 | 0.072 | 0.018 | 0.36 |
| Lactose | 1.2391 | 4.9564 | 0.2391 | 4.782 |
| Glucose anhydrous | 23.5429 | 94.1716 | 4.5429 | 90.858 |
| TOTAL 24- | 25 | | 5 | |
| Fluticasone | 0.05 | 0.2 | 0.05 | 1 |
| Indacaterol | 0.15 | 0.6 | 0.15 | 3 |
| Tiotropium | 0.018 | 0.072 | 0.018 | 0.36 |
| Glucose anhydrous | 1.2391 | 4.9564 | 0.2391 | 4.782 |
| Lactose | 23.5429 | 94.1716 | 4.5429 | 90.858 |
| TOTAL 25- | 25 | | 5 | |
| Budesonide | 0.2 | 0.8 | 0.2 | 4 |
| Indacaterol | 0.15 | 0.6 | 0.15 | 3 |
| Tiotropium | 0.018 | 0.072 | 0.018 | 0.36 |
| Lactose | 1.2316 | 4.9264 | 0.2316 | 4.632 |
| Glucose anhydrous | 23.4004 | 93.6016 | 4.4004 | 88.008 |
| TOTAL 26- | 25 | | 5 | |
| Budesonide | 0.2 | 0.8 | 0.2 | 4 |
| Indacaterol | 0.15 | 0.6 | 0.15 | 3 |
| Tiotropium | 0.018 | 0.072 | 0.018 | 0.36 |
| Glucose anhydrous | 1.2316 | 4.9264 | 0.2316 | 4.632 |
| Lactose | 23.4004 | 93.6016 | 4.4004 | 88.008 |
| TOTAL 27- | 25 | | 5 | |
| Budesonide | 0.4 | 1.6 | 0.4 | 8 |
| Indacaterol | 0.15 | 0.6 | 0.15 | 3 |
| Tiotropium | 0.018 | 0.072 | 0.018 | 0.36 |
| Lactose | 1.2216 | 4.8864 | 0.2216 | 4.432 |
| Glucose anhydrous | 23.2104 | 92.8416 | 4.2104 | 84.208 |
| TOTAL 28- | 25 | | 5 | |
| Budesonide | 0.4 | 1.6 | 0.4 | 8 |
| Indacaterol | 0.15 | 0.6 | 0.15 | 3 |
| Tiotropium | 0.018 | 0.072 | 0.018 | 0.36 |
| Glucose anhydrous | 1.2216 | 4.8864 | 0.2216 | 4.432 |
| Lactose | 23.2104 | 92.8416 | 4.2104 | 84.208 |
| TOTAL 29- | 25 | | 5 | |
| Budesonide | 0.2 | 0.8 | 0.2 | 4 |
| Olodeterol | 0.005 | 0.02 | 0.005 | 0.1 |
| Tiotropium | 0.018 | 0.072 | 0.018 | 0.36 |
| Lactose | 1.23885 | 4.9554 | 0.23885 | 4.777 |
| Glucose anhydrous | 23.53815 | 94.1526 | 4.53815 | 90.763 |
| TOTAL 30- | 25 | | 5 | |
| Budesonide | 0.2 | 0.8 | 0.2 | 4 |
| Olodeterol | 0.005 | 0.02 | 0.005 | 0.1 |
| Tiotropium | 0.018 | 0.072 | 0.018 | 0.36 |
| Glucose anhydrous | 1.23885 | 4.9554 | 0.23885 | 4.777 |
| Lactose | 23.53815 | 94.1526 | 4.53815 | 90.763 |
| TOTAL 31- | 25 | | 5 | |
| Budesonide | 0.4 | 1.6 | 0.4 | 8 |
| Olodeterol | 0.005 | 0.02 | 0.005 | 0.1 |
| Tiotropium | 0.018 | 0.072 | 0.018 | 0.36 |
| Lactose | 1.22885 | 4.9154 | 0.22885 | 4.577 |
| Glucose anhydrous | 23.34815 | 93.3926 | 4.34815 | 86.963 |
| TOTAL 32- | 25 | | 5 | |
| Budesonide | 0.4 | 1.6 | 0.4 | 8 |
| Olodeterol | 0.005 | 0.02 | 0.005 | 0.1 |
| Tiotropium | 0.018 | 0.072 | 0.018 | 0.36 |
| Glucose anhydrous | 1.22885 | 4.9154 | 0.22885 | 4.577 |
| Lactose | 23.34815 | 93.3926 | 4.34815 | 86.963 |
| TOTAL 33- | 25 | | 5 | |
| Budesonide | 0.2 | 0.8 | 0.2 | 4 |
| Vilanterol | 0.025 | 0.1 | 0.025 | 0.5 |
| Tiotropium | 0.018 | 0.072 | 0.018 | 0.36 |
| Lactose | 1.23785 | 4.9514 | 0.23785 | 4.757 |
| Glucose anhydrous | 23.51915 | 94.0766 | 4.51915 | 90.383 |
| TOTAL 34- | 25 | | 5 | |
| Budesonide | 0.2 | 0.8 | 0.2 | 4 |
| Vilanterol | 0.025 | 0.1 | 0.025 | 0.5 |
| Tiotropium | 0.018 | 0.072 | 0.018 | 0.36 |
| Glucose anhydrous | 1.23785 | 4.9514 | 0.23785 | 4.757 |
| Lactose | 23.51915 | 94.0766 | 4.51915 | 90.383 |
| TOTAL 35- | 25 | | 5 | |
| Budesonide | 0.4 | 1.6 | 0.4 | 8 |
| Vilanterol | 0.025 | 0.1 | 0.025 | 0.5 |
| Tiotropium | 0.018 | 0.072 | 0.018 | 0.36 |
| Lactose | 1.22785 | 4.9114 | 0.22785 | 4.557 |
| Glucose anhydrous | 23.32915 | 93.3166 | 4.32915 | 86.583 |
| TOTAL 36- | 25 | | 5 | |
| Budesonide | 0.4 | 1.6 | 0.4 | 8 |
| Vilanterol | 0.025 | 0.1 | 0.025 | 0.5 |
| Tiotropium | 0.018 | 0.072 | 0.018 | 0.36 |
| Lactose | 1.22785 | 4.9114 | 0.22785 | 4.557 |
| Glucose anhydrous | 23.32915 | 93.3166 | 4.32915 | 86.583 |
| TOTAL 37- | 25 | | 5 | |
| Mometasone | 0.1 | 0.4 | 0.1 | 2 |
| Indacaterol | 0.15 | 0.6 | 0.15 | 3 |
| Glikoporonyum | 0.1 | 0.4 | 0.1 | 2 |
| Lactose | 1.2325 | 4.93 | 0.2325 | 4.65 |
| Glucose anhydrous | 23.4175 | 93.67 | 4.4175 | 88.35 |
| TOTAL | 25 | | 5 | |

38-

| Ingredient | | | | |
|---|---|---|---|---|
| Mometasone | 0.1 | 0.4 | 0.1 | 2 |
| Indacaterol | 0.15 | 0.6 | 0.15 | 3 |
| Glikoporonyum | 0.1 | 0.4 | 0.1 | 2 |
| Glucose anhydrous | 1.2325 | 4.93 | 0.2325 | 4.65 |
| Lactose | 23.4175 | 93.67 | 4.4175 | 88.35 |
| TOTAL | 25 | | 5 | |

39-

| Ingredient | | | | |
|---|---|---|---|---|
| Mometasone | 0.2 | 0.8 | 0.2 | 4 |
| Indacaterol | 0.15 | 0.6 | 0.15 | 3 |
| Glikoporonyum | 0.1 | 0.4 | 0.1 | 2 |
| Lactose | 1.2275 | 4.91 | 0.2275 | 4.55 |
| Glucose anhydrous | 23.3225 | 93.29 | 4.3225 | 86.45 |
| TOTAL | 25 | | 5 | |

40-

| Ingredient | | | | |
|---|---|---|---|---|
| Mometasone | 0.2 | 0.8 | 0.2 | 4 |
| Indacaterol | 0.15 | 0.6 | 0.15 | 3 |
| Glikoporonyum | 0.1 | 0.4 | 0.1 | 2 |
| Glucose anhydrous | 1.2275 | 4.91 | 0.2275 | 4.55 |
| Lactose | 23.3225 | 93.29 | 4.3225 | 86.45 |
| TOTAL | 25 | | 5 | |

41-

| Ingredient | | | | |
|---|---|---|---|---|
| Fluticasone | 0.1 | 0.4 | 0.1 | 2 |
| Salmeterol | 0.05 | 0.2 | 0.05 | 1 |
| Salbutamol | 0.1 | 0.4 | 0.1 | 2 |
| Lactose | 1.2375 | 4.95 | 0.2375 | 4.75 |
| Glucose anhydrous | 23.5125 | 94.05 | 4.5125 | 90.25 |
| TOTAL | 25 | | 5 | |

42-

| Ingredient | | | | |
|---|---|---|---|---|
| Fluticasone | 0.1 | 0.4 | 0.1 | 2 |
| Salmeterol | 0.05 | 0.2 | 0.05 | 1 |
| Salbutamol | 0.1 | 0.4 | 0.1 | 2 |
| Glucose anhydrous | 1.2375 | 4.95 | 0.2375 | 4.75 |
| Lactose | 23.5125 | 94.05 | 4.5125 | 90.25 |
| TOTAL | 25 | | 5 | |

43-

| Ingredient | | | | |
|---|---|---|---|---|
| Fluticasone | 0.25 | 1 | 0.25 | 5 |
| Salmeterol | 0.05 | 0.2 | 0.05 | 1 |
| Salbutamol | 0.1 | 0.4 | 0.1 | 2 |
| Lactose | 1.23 | 4.92 | 0.23 | 4.6 |
| Glucose anhydrous | 23.37 | 93.48 | 4.37 | 87.4 |
| TOTAL | 25 | | 5 | |

44-

| Ingredient | | | | |
|---|---|---|---|---|
| Fluticasone | 0.25 | 1 | 0.25 | 5 |
| Salmeterol | 0.05 | 0.2 | 0.05 | 1 |
| Salbutamol | 0.1 | 0.4 | 0.1 | 2 |
| Glucose anhydrous | 1.23 | 4.92 | 0.23 | 4.6 |
| Lactose | 23.37 | 93.48 | 4.37 | 87.4 |
| TOTAL | 25 | | 5 | |

45-

| Ingredient | | | | |
|---|---|---|---|---|
| Fluticasone | 0.5 | 2 | 0.5 | 10 |
| Salmeterol | 0.05 | 0.2 | 0.05 | 1 |
| Salbutamol | 0.1 | 0.4 | 0.1 | 2 |
| Lactose | 1.2175 | 4.87 | 0.2175 | 4.35 |
| Glucose anhydrous | 23.1325 | 92.53 | 4.1325 | 82.65 |
| TOTAL | 25 | | 5 | |

46-

| Ingredient | | | | |
|---|---|---|---|---|
| Fluticasone | 0.5 | 2 | 0.5 | 10 |
| Salmeterol | 0.05 | 0.2 | 0.05 | 1 |
| Salbutamol | 0.1 | 0.4 | 0.1 | 2 |
| Glucose anhydrous | 1.2175 | 4.87 | 0.2175 | 4.35 |
| Lactose | 23.1325 | 92.53 | 4.1325 | 82.65 |
| TOTAL | 25 | | 5 | |

47-

| Ingredient | | | | |
|---|---|---|---|---|
| Fluticasone | 0.1 | 0.4 | 0.1 | 2 |
| Arformeterol | 0.015 | 0.06 | 0.015 | 0.3 |
| Salbutamol | 0.1 | 0.4 | 0.1 | 2 |
| Lactose | 1.23925 | 4.957 | 0.23925 | 4.785 |
| Glucose anhydrous | 23.54575 | 94.183 | 4.54575 | 90.915 |
| TOTAL | 25 | | 5 | |

48-

| Ingredient | | | | |
|---|---|---|---|---|
| Fluticasone | 0.1 | 0.4 | 0.1 | 2 |
| Arformeterol | 0.015 | 0.06 | 0.015 | 0.3 |
| Salbutamol | 0.1 | 0.4 | 0.1 | 2 |
| Glucose anhydrous | 1.23925 | 4.957 | 0.23925 | 4.785 |
| Lactose | 23.54575 | 94.183 | 4.54575 | 90.915 |
| TOTAL | 25 | | 5 | |

49-

| Ingredient | | | | |
|---|---|---|---|---|
| Fluticasone | 0.25 | 1 | 0.25 | 5 |
| Arformeterol | 0.015 | 0.06 | 0.015 | 0.3 |
| Salbutamol | 0.1 | 0.4 | 0.1 | 2 |
| Lactose | 1.23175 | 4.927 | 0.23175 | 4.635 |
| Glucose anhydrous | 23.40325 | 93.613 | 4.40325 | 88.065 |
| TOTAL | 25 | | 5 | |

50-

| Ingredient | | | | |
|---|---|---|---|---|
| Fluticasone | 0.25 | 1 | 0.25 | 5 |
| Arformeterol | 0.015 | 0.06 | 0.015 | 0.3 |
| Salbutamol | 0.1 | 0.4 | 0.1 | 2 |
| Glucose anhydrous | 1.23175 | 4.927 | 0.23175 | 4.635 |
| Lactose | 23.40325 | 93.613 | 4.40325 | 88.065 |
| TOTAL | 25 | | 5 | |

51-

| Ingredient | | | | |
|---|---|---|---|---|
| Fluticasone | 0.5 | 2 | 0.5 | 10 |
| Arformeterol | 0.015 | 0.06 | 0.015 | 0.3 |
| Salbutamol | 0.1 | 0.4 | 0.1 | 2 |
| Lactose | 1.21925 | 4.877 | 0.21925 | 4.385 |
| Glucose anhydrous | 23.16575 | 92.663 | 4.16575 | 83.315 |
| TOTAL | 25 | | 5 | |

52-

| Ingredient | | | | |
|---|---|---|---|---|
| Fluticasone | 0.5 | 2 | 0.5 | 10 |
| Arformeterol | 0.015 | 0.06 | 0.015 | 0.3 |
| Salbutamol | 0.1 | 0.4 | 0.1 | 2 |
| Glucose anhydrous | 1.21925 | 4.877 | 0.21925 | 4.385 |
| Lactose | 23.16575 | 92.663 | 4.16575 | 83.315 |
| TOTAL | 25 | | 5 | |

Compositions according to the invention are manufactured by the processes of the state of art in such a way that they include mixtures of fine particle lactose-coarse particle glucose anhydrous, fine particle glucose anhydrous-coarse particle lactose and the active ingredients.

For fine particle carriers (lactose or glucose anhydrous) might be in the range of:
d10; 1.0-5.0 µm or d10; 1.0-4.0 µm,
d50; 4.0-10.0 µm or d50; 4.0-7.0 µm,
d90; 7.0-20.0 µm or d90; 7.0-15.0 µm.

For coarse particle carriers (lactose or glucose anhydrous) might be in the range of:
d10; 10.0-50.0 µm
d50; 50.0-120.0 µm or d50; 50.0-75.0 µm,
d90; 120.0-300.0 µm or d90; 75.0-250.0 µm.

Said compositions may be formed as:
i. Active ingredient+fine particle lactose+coarse particle glucose anhydrous,
ii. Active ingredient+fine particle lactose+coarse particle lactose,
iii. Active ingredient+fine particle lactose+fine particle glucose anhydrous+coarse particle glucose anhydrous,
iv. Active ingredient+fine particle lactose+fine particle glucose anhydrous+coarse particle lactose,
v. Active ingredient+fine particle lactose+coarse particle glucose anhydrous+coarse particle lactose,
vi. Active ingredient+fine particle lactose+fine particle glucose anhydrous+coarse particle glucose anhydrous+coarse particle lactose.

Surprisingly, said glucose anhydrous in the invention increases stability by absorbing moisture to it contained in the active ingredients inside the blister having air and moisture barriers or the airtight and moisture-tight capsule. Dehumidification of the active ingredient or ingredients bring the stability values to desired level. Furthermore, by means of ideal lactose and glucose anhydrous ratio and their determined particle sizes, compositions with content uniformity are developed. In addition to this, dosage accuracy present in each cavity or capsule is ensured as well. These preferred values facilitate the flowing and filling of the components as well, during the process. It is ensured that a homogeneous mixture is obtained and this filling is economical and fast.

Coarse carrier particles are used in or order to prevent agglomeration (anew) of the fine particles of the active ingredient. In order to obtain this effect, a carrier, the particle size of which is 10 times that of the active ingredient is used. In general, a single layer composed of the active ingredient particles is formed over the large carrier particles. During inhalation, as the active ingredient and the carrier substance need to be separated from each other, shape and surface roughness of the carrier particles are especially important. Particles of smooth surface will be separated much easier from the active ingredient compared to the particles in the same size but of high porosity.

Fine carrier particles are used so as to assist the active ingredient to reach to the lungs safer and in high doses. Active ingredient will tend to concentrate on the regions having higher energy as the surface energy normally does not dissipate on the carrier particle evenly. This might obstruct the active ingredient to separate from the carrier after pulmonary administration, especially in low dose formulations. As the high-energy regions will be covered by fine carrier particles and thus the active ingredient will tend to bind to low energy regions, usage of small fine carrier particles, size of which are less than 10.0 microns or 5.0 microns will help to prevent this situation. It has been discovered that by increasing the fraction of the fine carrier particles, taking into lungs will also increase. According to this, a decrease in the particle size (having finer particles) increases the fluidizing energy and this, in return, increases the amount of drug reached to the lungs.

Drug particles will adhere then to weak adhesion regions and will be released easier during inhalation. Surface area will significantly increase upon addition of fine particles and carrying capacity will decrease. The fact that the fine carrier particles are slightly coarser than the drug particles is sufficient to eliminate the frictional forces between the drug and the carrier during mixing process.

Another object of the invention is to adjust the fluidity of the formulations accurately in order to ensure that correct amounts of active ingredient are given to the DPIs by suitable devices. In other words, present invention provides freely-flowable formulations by choosing right carriers in order to ensure continuous production of formulations, mechanical filling of the powder inhaler, right dosage and release with powder inhaler.

Another object of the invention is to prevent agglomeration by using a suitable carrier except lactose. Active particles have fine or sometimes micro-fine particles in order to be able to penetrate deep into lungs. For this reason, these small drug particles tend to agglomerate.

In an ideal drug carrier system, binding of the active ingredient to the carrier should be as strong as to prevent decaying of the mixture yet it should be so strong as the active ingredient and the carrier need to separate during inhalation. Accordingly, shape of the carrier particles and surface roughness are of particular importance. Spray-dried glucose anhydrous particles are observed to detach from the active ingredient easier in comparison with the particles of high porosity in same size. Since, spray-dried glucose anhydrous forms more particles of spherical shape and a smooth surface. The characteristic of such particles is that they have a smaller contact area and a smaller and more homogeneous particle size distribution, which leads the inhalable particles to be more, compared to the carriers the diameters of which are diminished mechanically. An advantage of using spray-dried glucose anhydrous is to obtain particles in which the particle size distribution is narrow and the diameters are of a few micrometers. And this ensures the drug embedded in the trachea-bronchial and deep alveoli regions to be stored at maximum ratios by normal inhalation rate, once the suitable particle size is obtained. Furthermore, spray-dried glucose anhydrous exhibits narrow particle size, i.e., the ratio between the particle size (d50) and (d90) is equal to 0.40 or greater. The ratio between the (d50) particle size and d90 is preferably between 0.45 and 0.50, more preferably between 0.50 and 0.70.

In addition to this, this narrow particle size distribution that is equal to 0.40 or greater applies also to glucose anhydrous contained in the compositions of present invention. Preferably, narrow particle size distribution is between 0.45 and 0.50, more preferably between 0.50 and 0.70.

Particle size analysis is performed by MALVERN MASTERSIZER 200™ (a device for determining particle size based on laser diffraction) with laser diffraction technique. According to selected active ingredient may prefer particle characterization techniques that it can be wet dispersion (particles dispersed in a liquid) or dry dispersion (particles dispersed in a gas (usually air)). Particle size distribution measure volume-basis.

According to a preferred embodiment of the invention, therapeutically active amount of said pharmaceutical compositions is administered once a day and/or twice a day.

According to a preferred embodiment, pharmaceutical compositions are used in the treatment of the respiratory diseases selected from asthma and chronic obstructive pulmonary disease and other obstructive respiratory diseases. Combinations of present invention are particularly useful in the treatment of the respiratory diseases or disorders including asthma, acute respiratory failure, chronic pulmonary inflammatory disease, bronchitis, chronic bronchitis, chronic obstructive pulmonary disease and silicosis or immune diseases and disorders including allergic rhinitis or chronic sinusitis.

According to another application, pharmaceutical compositions are suitable for separate, respective or simultaneous administration with a blister resistant to moisture and encapsulated with a secure barrier or with a capsule.

Blister especially contains aluminum in order to prevent moisture intake and thereby fine particle fraction (FPF) of the dose of the pharmaceutical composition is maintained. Blister is further encapsulated with a secure barrier resistant to moisture. By this means, blister prevents water penetration into the drug dose and moisture intake from outside into the container has been prevented.

In another preferred embodiment of the invention, dry powder is inside a capsule and this capsule may be a gelatin or a natural or synthetic pharmaceutically acceptable polymer such as hydroxypropyl methylcellulose.

Dosage amounts of 25 mg are stored inside air-tight and moisture-tight capsules, whereas dosage amounts of 5 mf are stored inside blisters.

Moreover, as said formulas may contain active ingredient in amounts of 3 or 5 mg alone or else in the amounts that are the multiples of 3 or 5 mg, it is also possible to manufacture combinations of said active ingredient comprising the amounts of 3 or 5 mg or else that are the multiples of 3 or 5 mg.

A pharmaceutically acceptable salt, solvate, polymorph or racemic mixture of said active ingredient may also be used.

Said ciclesonide may contain pharmaceutically acceptable salt, solvate, polymorph or racemic mixture thereof.

Said budesonide may contain pharmaceutically acceptable salt, solvate, polymorph or racemic mixture thereof.

As said fluticasone may contain pharmaceutically acceptable salt, solvate, polymorph or racemic mixture thereof, it is preferably propionate or fluticasone furoate.

As said mometasone may contain pharmaceutically acceptable salt, solvate, polymorph or racemic mixture thereof, it is preferably mometasone furoate or mometasone furoate anhydrate.

As said tiotropium may contain pharmaceutically acceptable salt, solvate, polymorph or racemic mixture thereof, it is preferably tiotropium bromide.

As said glycopyrronium may contain pharmaceutically acceptable salt, solvate, polymorph or racemic mixture thereof, it is preferably glycopyrronium bromide.

Said aclinidium may contain pharmaceutically acceptable salt, solvate, polymorph or racemic mixture thereof.

As said darotropium may contain pharmaceutically acceptable salt, solvate, polymorph or racemic mixture thereof, it is preferably darotropium bromide.

As said salmaterol may contain pharmaceutically acceptable salt, solvate, polymorph or racemic mixture thereof, it is preferably salmeterol xinafoate.

As said formoterol may contain pharmaceutically acceptable salt, solvate, polymorph or racemic mixture thereof, it is preferably formoterol fumarate.

As said arfomoterol may contain pharmaceutically acceptable salt, solvate, polymorph or racemic mixture thereof, it is preferably arfomoterol tartrarate.

As said indacaterol may contain pharmaceutically acceptable salt, solvate, polymorph or racemic mixture thereof, it is preferably indacaterol maleate.

Said salbutamol may contain pharmaceutically acceptable salt, solvate, polymorph or racemic mixture thereof.

Said vilanterol may contain pharmaceutically acceptable salt, solvate, polymorph or racemic mixture thereof.

Said carmoterol may contain pharmaceutically acceptable salt, solvate, polymorph or racemic mixture thereof.

Said olodaterol may contain pharmaceutically acceptable salt, solvate, polymorph or racemic mixture thereof.

Said compositions are inserted in a dry powder inhaler device containing a blister and a cap. Said device has at least one locking mechanism ensuring the device to be maintained locked in both of the positions in which it is ready for inhalation and its cap is closed and ensuring the device to be automatically re-set once the cap is closed.

Subsequent to opening of the device cap, a force is exerted to the device cock by the user. Afterwards, the cock is bolted by being guided by the tracks within the body of the device and the tracks on itself. Mechanism is assured to function via this action. In the end of bolting, cock is locked upon clamping and single dose drug come out of the blister is enabled to be administered. Pushing of the cock by the user completely until the locking position ensures the blister to be completely peeled off and the dosage amount to be accurately administered. As a result of this locking cock is immobilized and is disabled for a short time. This pushing action further causes the spring inside the mechanism to be compressed between the cock and the inner body of the device. Said device becomes ready to re-use following the closing of the cap by the user after the administration of the powder composition, without needing to be set again, thanks to the mechanism involved.

When said compositions are used in a dry powder inhaler comprising capsule, said capsule is put one by one in the device and used by means of exploding the capsule.

The invention claimed is:

1. A dry powder inhalation composition comprising, at least one corticosteroid or a pharmaceutically acceptable salt thereof, fine particle lactose in an amount of 1-20% by weight of said composition and having d50 particle size in the range of 4-10 μm and coarse particle anhydrous glucose in an amount of 80-99% by weight of said composition and having a d50 particle size in the range of 50-120 μm.

2. The pharmaceutical composition according to claim 1, wherein the d50 particle size of said fine particle lactose is 4-7 μm.

3. The pharmaceutical composition according to claim 1, wherein a d50 particle size of said coarse particle anhydrous glucose is 50-75 μm.

4. The pharmaceutical composition according to claim 1, further comprising coarse particle lactose with a d50 particle size of 50-80 μm or of 50-75 μm, coarse particle lactose with a d10 particle size of 10-50 μm, and/or coarse particle lactose with a d90 particle size of 120-300 μm or 75-250 μm.

5. The pharmaceutical composition according to claim 1, further comprising fine particle anhydrous glucose with a d50 particle size of 4-7 μm, fine particle anhydrous glucose with a d10 particle size of 1-5 μm or 1-4 μm; and/or fine particle anhydrous glucose with a d90 particle size of 10-20 μm or 7-10 μm.

6. The pharmaceutical composition according to claim 1, wherein the amount of said lactose is in the range of 1-15%, or 1-10%, by weight.

7. The pharmaceutical composition according to claim 1, wherein the amount of said anhydrous glucose is in the range of 85-99%, or 90-99%, by weight of the composition.

8. The pharmaceutical composition according to claim 1, wherein, said corticosteroid is selected from the group consisting of at least one or a mixture of ciclesonide, budesonide, fluticasone, aldosterone, beclomethasone, betametazone, chloprednol, cortisone, cortivasol, deoxycortone, desonide, desoxymethasone, dexamethasone, difluocortolone, fluchloralin, flumetasone, flunisolide, fluocinolone, fluocinonide, flurocortisone, fluocortolone, flurometolone, flurandrenolone, halcinonide, hydrocortisone, icometasone, meprednisone, methylprednisolone, mometasone, paramethasone, prednisolone, prednisone, tixocortole, and/or triamcinolone.

9. The pharmaceutical composition according to claim 8, wherein, said corticosteroid is selected from the group consisting of ciclesonide, budesonide, fluticasone, and mometasone.

10. The pharmaceutical composition according to claim 1, further comprising (a) one or more β2-adrenergic agonists; (b) one or more muscarinic receptor antagonists; or (c) one or more β2-adrenergic agonists and one or more muscarinic receptor antagonists.

11. The pharmaceutical composition according to claim 10, wherein said muscarinic receptor antagonist is selected from the group consisting of at least one or a mixture of tiotropium, glycopyrronium, aclidinium, darotropium, and ipratropium.

12. The pharmaceutical composition according to claim 10, wherein, said beta-2 adrenergic agonist is selected from the group consisting of at least one or a mixture of salmeterol, formoterol, arformoterol, salbutamol, indacaterol, terbutaline, metaproterenol, vilanterol, carmoterol, olodaterol, bambuterol, and clenbuterol.

13. The pharmaceutical composition according to claim 1, further comprising at least one excipient selected from the group consisting of glucose, mannitol, sorbitol, trehalose, and cellobiose.

14. The pharmaceutical composition according to claim 1, wherein, said composition comprises one of the following therapeutically active combinations:
  i. Budesonide and indacaterol,
  ii. Budesonide and oladaterol,
  iii. Budesonide and vilanterol,
  iv. Budesonide and salmeterol,
  v. Budesonide and formoterol,
  vi. Budesonide and carmoterol,
  vii. Budesonide and arformoterol,
  viii. fluticasone and formoterol,
  ix. fluticasone and salmeterol,
  x. fluticasone and vilanterol,
  xi. fluticasone and indacaterol,
  xii. fluticasone and olodaterol,
  xiii. fluticasone and carmoterol,
  xiv. fluticasone and arformoterol,
  xv. fluticasone and salbutamol,
  xvi. mometasone and formoterol,
  xvii. mometasone and indacaterol,
  xviii. mometasone and vilanterol,
  xix. mometasone and olodaterol,
  xx. mometasone and carmoterol,
  xxi. mometasone and arformoterol,
  xxii. mometasone and salmeterol,
  xxiii. ciclesonide and formoterol,
  xxiv. ciclesonide and vilanterol,
  xxv. ciclesonide and indacaterol,
  xxvi. ciclesonide and olodaterol,
  xxvii. ciclesonide and carmoterol,
  xxviii. ciclesonide and arformoterol,
  xxix. ciclesonide and salmeterol,
  xxx. budesonide and tiotropium,
  xxxi. fluticasone and tiotropium,
  xxxii. mometason and tiotropium,
  xxxiii. ciclesonide and tiotropium,
  xxxiv. budesonide, formoterol and tiotropium,
  xxxv. budesonide, salmeterol and tiotropium,
  xxxvi. budesonide, arformoterol and tiotropium,
  xxxvii. budesonide, carmoterol and tiotropium,
  xxxviii. ciclesonide, formoterol and tiotropium,
  xxxix. ciclesonide, salmeterol and tiotropium,
  xl. ciclesonide, carmoterol and tiotropium,
  xli. ciclesonide, arformoterol and tiotropium,
  xlii. ciclesonide, indacaterol and tiotropium,
  xliii. ciclesonide, olodaterol and tiotropium,
  xliv. ciclesonide, vilanterol and tiotropium,
  xlv. fluticasone, salmeterol and tiotropium,
  xlvi. fluticasone, formoterol and tiotropium,
  xlvii. fluticasone, arfomoterol and tiotropium,
  xlviii. fluticasone, carmoterol and tiotropium,
  xlix. fluticasone, vilanterol and tiotropium,
  l. fluticasone, olodaterol and tiotropium,
  li. fluticasone, indacaterol and tiotropium,
  lii. budesonide, indacaterol and tiotropium,
  liii. budesonide, olodaterol and tiotropium,
  liv. budesonide, vilanterol and tiotropium,
  lv. mometasone, salmeterol and tiotropium,
  lvi. mometasone, formoterol and tiotropium,
  lvii. mometasone, indacaterol and tiotropium,
  lviii. mometasone, vilanterol and tiotropium,
  lix. mometasone, oladaterol and tiotropium,
  lx. mometasone, arformoterol and tiotropium,
  lxi. mometasone, indacaterol and glycopyrronium,
  lxii. mometasone, salmeterol and glycopyrronium,
  lxiii. mometasone, formoterol and glycopyrronium,
  lxiv. mometasone, carmoterol and glycopyrronium,
  lxv. mometasone, olodaterol and glycopyrronium,
  lxvi. mometasone, vilanterol and glycopyrronium,
  lxvii. fluticasone, salmeterol and salbutamol, and
  lxviii. fluticasone, arformeterol and salbutamol.

15. The pharmaceutical composition according to claim 1, wherein said composition is in a blister having air and moisture barrier property, enabling simultaneous, respective and synchronic application.

16. The pharmaceutical composition according to claim 1, wherein said composition is in a blister in a dry powder inhaler device suitable for simultaneous, respective and synchronic application, wherein the inhaler device has at least one locking mechanism ensuring the device to be maintained locked in both of the positions in which the inhaler device is ready for inhalation and the lid of the inhaler device is closed and ensuring the device to be automatically re-set once the lid is closed.

17. The pharmaceutical composition according to claim 1, wherein, said composition comprises a dry powder inhaler device suitable for simultaneous, respective and synchronic application in a capsule.

18. The pharmaceutical composition according to claim 1, wherein the coarse particle anhydrous glucose has a ratio of the d50 particle size/d90 particle size equal to 0.40 or greater.

19. The pharmaceutical composition according to claim 1, wherein the coarse particle anhydrous glucose has a ratio of the d50 particle size/d90 particle size between 0.45 and 0.50.

20. The pharmaceutical composition according to claim 1, wherein the coarse particle anhydrous glucose has a ratio of the d50 particle size/d90 particle size between 0.50 and 0.70.

21. The pharmaceutical composition according to claim 18, wherein the coarse particle anhydrous glucose comprises spray-dried anhydrous glucose.

22. The pharmaceutical composition according to claim 19, wherein the coarse particle anhydrous glucose comprises spray-dried anhydrous glucose.

23. The pharmaceutical composition according to claim 20, wherein the coarse particle anhydrous glucose comprises spray-dried anhydrous glucose.

24. The pharmaceutical composition according to claim 3, wherein the coarse particle anhydrous glucose has a ratio of the d50 particle size/d90 particle size equal to 0.40 or greater.

25. The pharmaceutical composition according to claim 3, wherein the coarse particle anhydrous glucose has a ratio of the d50 particle size/d90 particle size between 0.45 and 0.50.

26. The pharmaceutical composition according to claim 3, wherein the coarse particle anhydrous glucose has a ratio of the d50 particle size/d90 particle size between 0.50 and 0.70.

27. The pharmaceutical composition according to claim 1, wherein said fine particle lactose has a d10 particle size of 1-5 μm.

28. The pharmaceutical composition according to claim 1, wherein said fine particle lactose has a d90 particle size of 7-20 μm.

29. The pharmaceutical composition according to claim 1, wherein said coarse particle anhydrous glucose has a d10 particle size of 10-50 μm.

30. The pharmaceutical composition according to claim 1, wherein said coarse particle anhydrous glucose has a d90 particle size of 120-300 μm.

31. The pharmaceutical composition according to claim 27, wherein said fine particle lactose has a d10 particle size of 1-4 μm.

32. The pharmaceutical composition according to claim 28, wherein said fine particle lactose has a d90 particle size of 7-15 μm.

33. The pharmaceutical composition according to claim 30, wherein said coarse particle anhydrous glucose has a d90 particle size of 75-250 μm.

34. The pharmaceutical composition according to claim 29, wherein said coarse particle anhydrous glucose has a d90 particle size of 75-250 μm.

* * * * *